(12) United States Patent
Fu

(10) Patent No.: US 8,252,558 B2
(45) Date of Patent: Aug. 28, 2012

(54) METHODS FOR AMPLIFYING AND DETECTING NUCLEIC ACID SEQUENCES

(75) Inventor: Guoliang Fu, Oxford (GB)

(73) Assignee: Oxitec Limited, Abingdon, Oxford, Oxfordshire (GB)

( * ) Notice: Subject to any disclaimer, the term of this patent is extended or adjusted under 35 U.S.C. 154(b) by 369 days.

(21) Appl. No.: 12/444,995

(22) PCT Filed: Oct. 5, 2007

(86) PCT No.: PCT/GB2007/003793
§ 371 (c)(1),
(2), (4) Date: Apr. 9, 2009

(87) PCT Pub. No.: WO2008/043987
PCT Pub. Date: Apr. 17, 2008

(65) Prior Publication Data
US 2010/0105037 A1    Apr. 29, 2010

(30) Foreign Application Priority Data

| Oct. 9, 2006 | (GB) | 0619951.7 |
| Jan. 10, 2007 | (GB) | 0700461.7 |
| Feb. 12, 2007 | (GB) | 0702692.5 |
| Mar. 15, 2007 | (GB) | 0705029.7 |

(51) Int. Cl.
*C12P 19/34* (2006.01)
(52) U.S. Cl. .................................................. 435/91.2
(58) Field of Classification Search ................. None
See application file for complete search history.

(56) References Cited

U.S. PATENT DOCUMENTS

| 6,027,923 A * | 2/2000 | Wallace .................... 435/91.2 |
| 6,335,184 B1 * | 1/2002 | Reyes et al. ................ 435/91.2 |
| 6,632,641 B1 * | 10/2003 | Brennan et al. ................. 506/9 |
| 2003/0228596 A1 * | 12/2003 | Liu et al. ......................... 435/6 |
| 2006/0094033 A1 | 5/2006 | Abulencia et al. | |

FOREIGN PATENT DOCUMENTS

| EP | 1420069 | 5/2004 |
| EP | 1568786 | 8/2005 |
| WO | 99/18241 | 4/1999 |
| WO | 03/033724 | 4/2003 |
| WO | 03/074724 | 9/2003 |
| WO | WO 03074724 A2 * | 9/2003 |
| WO | 2004/013354 | 2/2004 |
| WO | 2005/012499 | 2/2005 |

OTHER PUBLICATIONS

Solinas, A. et al., "Duplex scorpion primers in SNP analysis and FRET applications," Nuc. Acids Res. (2001) 29(20): E96 (9 pages).
Walker, T.G. et al., "Isothermal in vitro amplification of DNA by a restriction enzyme/DNA polymerase system," Proc. Natl. Acad. Sci. USA (1992) 89(1):392-396.
International Search Report and Written Opinion for Application No. PCT/GB2007/003793 dated Jul. 21, 2008 (19 pages).

* cited by examiner

*Primary Examiner* — Christopher M. Babic
(74) *Attorney, Agent, or Firm* — Andrus, Sceales, Starke & Sawall, LLP

(57) ABSTRACT

The present invention, in different aspects and embodiments, provides nucleic acid amplification and detection methods that are both sensitive and fast. In various aspects there are disclosed amplification methods employing different combinations of primers to which can achieve exponential amplification and strand displacement, such as to generate a more than two fold increase of the amount of a target nucleic acid sequence during repeated cycles, while additionally permitting the production of single stranded products. Also provided are detection systems and kits.

23 Claims, 15 Drawing Sheets

Single stranded end products

Interaction of probes and single-stranded end products

A

B

|  |  |  |  |  |
|---|---|---|---|---|
| Inner primer K10F2a | + | + | + | + |
| Inner primer K10F3a | + | + | + | + |
| Outer primer K10F1 |  |  | + | + |
| Outer primer K10R4 |  |  | + | + |
| Cycle 94-58-72 (°C) | + |  | + |  |
| Cycle 94-58-72-58-72 (°C) |  | + |  | + |

A

B

SEQUENCE LISTING

<160> NUMBER OF SEQ ID NOS: 19

<210> SEQ ID NO 1
<211> LENGTH: 41
<212> TYPE: DNA
<213> ORGANISM: Artificial sequence
<220> FEATURE:
<223> OTHER INFORMATION: Synthetic sequence: degenerate primer
<220> FEATURE:
<221> NAME/KEY: misc_feature
<222> LOCATION: (29)..(37)
<223> OTHER INFORMATION: n is a or g or c or t

<400> SEQUENCE: 1
gtgtagcgtg aagacgacag aaagggcgnn nnnnnnntwt r                41

<210> SEQ ID NO 2
<211> LENGTH: 28
<212> TYPE: DNA
<213> ORGANISM: Artificial sequence

```
<220> FEATURE:
<223> OTHER INFORMATION: Synthetic sequence: "Universal primer"

<400> SEQUENCE: 2
gtgtagcgtg aagacgacag aaagggcg                                          28

<210> SEQ ID NO 3
<211> LENGTH: 782
<212> TYPE: DNA
<213> ORGANISM: Artificial sequence
<220> FEATURE:
<223> OTHER INFORMATION: Synthetic sequence: Target dna sequence K10
      3-primeUTR from a transgenic medfly line

<400> SEQUENCE: 3
ggagcttgat aacattatac ctaaacccat ggtcaagagt aaacatttct gcctttgaag        60
ttgagaacac aattaagcat cccctggtta aacctgacat tcatacttgt taatagcgcc      120
ataaacatag caccaatttc gaagaaatca gttaaaagca attagcaatt agcaattagc      180
aataactctg ctgacttcaa aacgagaaga gttgcaagta tttgtaaggc acagtttata      240
gaccaccgac ggctcattag ggctcgtcat gtaactaagc gcggtgaaac ccaattgaac      300
atatagtgga attattatta tcaatgggga agatttaacc ctcaggtagc aaagtaattt      360
aattgcaaat agagagtcct aagactaaat aatatattta aaaatctggc cctttgacct      420
tgcttgtcag gtgcatttgg gttcaatcgt aagttgcttc tatataaaca ctttccccat      480
ccccgcaata atgaagaata ccgcagaata aagagagatt tgcaacaaaa aataaaggca      540
ttgcgaaaac ttttttatggg ggatcattac actcgggcct acggttacaa ttcccagcca     600
cttaagcgac aagtttggcc aacaatccat ctaatagcta atagcgcaat cactggtaat      660
cgcaagagta tataggcaat agaacccatg gatttgacca aagtaaccg agacaatgga       720 gaagcaagag gatttcaaac tgaacaccca cagtactgtg tactaccact ggcgcgtttg      780
gg                                                                    782

<210> SEQ ID NO 4
<211> LENGTH: 26
<212> TYPE: DNA
<213> ORGANISM: Artificial sequence
<220> FEATURE:
<223> OTHER INFORMATION: Synthetic sequence: Primer K10F1

<400> SEQUENCE: 4
gcgccataaa catagcacca atttcg                                           26

<210> SEQ ID NO 5
<211> LENGTH: 25
<212> TYPE: DNA
<213> ORGANISM: Artificial sequence
<220> FEATURE:
<223> OTHER INFORMATION: Synthetic sequence:  Primer K10F2A

<400> SEQUENCE: 5
ggctcattag ggctcgtcat gtaac                                            25

<210> SEQ ID NO 6
<211> LENGTH: 25
<212> TYPE: DNA
<213> ORGANISM: Artificial sequence
<220> FEATURE:
<223> OTHER INFORMATION: Synthetic sequence:  Primer K10R3A

<400> SEQUENCE: 6
```
ccaaatgcac ctgacaagca aggtc                                          25

<210> SEQ ID NO 7
<211> LENGTH: 31
<212> TYPE: DNA
<213> ORGANISM: Artificial sequence
<220> FEATURE:
<223> OTHER INFORMATION: Synthetic sequence:  Primer K10R4

<400> SEQUENCE: 7
gcaaatctct ctttattctg cggtattctt c                                   31

<210> SEQ ID NO 8
<211> LENGTH: 49
<212> TYPE: DNA
<213> ORGANISM: Artificial sequence
<220> FEATURE:
<223> OTHER INFORMATION: Synthetic sequence: reverse inner linker -
      primer K10R4link

<400> SEQUENCE: 8
ggctcattag ggctcgtcat gtaacctgag ggttaaatct tccccattg                49

<210> SEQ ID NO 9
<211> LENGTH: 486
<212> TYPE: DNA
<213> ORGANISM: Homo sapiens

<400> SEQUENCE: 9
ggaaagcatc tcacctcatc ctaacacatt tcaagcccca aaaatcttaa aagcaggtta    60
tataggctaa atagaactaa tcattgtttt agacatactt attgactcta agaggaaaga   120
tgaagtacta tgttttaaag aatattatat tacagaatta tagaaattag atctcttacc   180
taaactcttc ataatgcttg ctctgatagg aaaatgagat ctactgtttt cctttactta   240
ctacacctca gatatatttc ttcatgaaga cctcacagta aaaataggtg attttggtct   300
agctacagtg aaatctcgat ggagtgggtc ccatcagttt gaacagttgt ctggatccat   360
tttgtggatg gtaagaattg aggctatttt tccactgatt aaattttgg ccctgagatg    420 ctgctgagtt actagaaagt cattgaaggt ctcaactata gtattttcat agttcccagt   480
attcac                                                              486

<210> SEQ ID NO 10
<211> LENGTH: 27
<212> TYPE: DNA
<213> ORGANISM: Artificial sequence
<220> FEATURE:
<223> OTHER INFORMATION: Synthetic sequence:  Primer BrafF2

<400> SEQUENCE: 10
ggaaagcatc tcacctcatc ctaacac                                        27

<210> SEQ ID NO 11
<211> LENGTH: 28
<212> TYPE: DNA
<213> ORGANISM: Artificial sequence
<220> FEATURE:
<223> OTHER INFORMATION: Synthetic sequence: Primer BrafEndR2

<400> SEQUENCE: 11
gactttctag taactcagca gcatctca                                       28

<210> SEQ ID NO 12
<211> LENGTH: 22

```
<212> TYPE: DNA
<213> ORGANISM: Artificial sequence
<220> FEATURE:
<223> OTHER INFORMATION: Synthetic sequence: Primer BrafFAMR2
<220> FEATURE:
<221> NAME/KEY: misc_feature
<222> LOCATION: (15)..(16)
<223> OTHER INFORMATION: dR-biotin
<220> FEATURE:
<221> NAME/KEY: misc_feature
<222> LOCATION: (21)..(22)
<223> OTHER INFORMATION: Phosphorothioate linkage

<400> SEQUENCE: 12
ggacccactc catcggattt ca                                              22

<210> SEQ ID NO 13
<211> LENGTH: 69
<212> TYPE: DNA
<213> ORGANISM: Artificial sequence
<220> FEATURE:
<223> OTHER INFORMATION: Synthetic sequence: linker-primer K10R4tlong

<400> SEQUENCE: 13
ggtggcgttg cggctggcgg agctcattag ggctcgtcat gtaacctgag ggttaaatct    60
tccccattg                                                             69

<210> SEQ ID NO 14
<211> LENGTH: 22
<212> TYPE: DNA
<213> ORGANISM: Artificial sequence
<220> FEATURE:
<223> OTHER INFORMATION: Synthetic sequence

<400> SEQUENCE: 14
ggtggcgttg cggctggcgg ag                                              22

<210> SEQ ID NO 15
<211> LENGTH: 27
<212> TYPE: DNA
<213> ORGANISM: Artificial sequence
<220> FEATURE:
<223> OTHER INFORMATION: Synthetic sequence: FamProbe

<400> SEQUENCE: 15
ctccgccagc cgcaacgcca ccgccag                                         27

<210> SEQ ID NO 16
<211> LENGTH: 23
<212> TYPE: DNA
<213> ORGANISM: Artificial sequence
<220> FEATURE:
<223> OTHER INFORMATION: Synthetic sequence: linker sequence

<400> SEQUENCE: 16
ctcattaggg ctcgtcatgt aac                                             23

<210> SEQ ID NO 17
<211> LENGTH: 46
<212> TYPE: DNA
<213> ORGANISM: Artificial sequence
<220> FEATURE:
<223> OTHER INFORMATION: Synthetic sequence: Primer K10F2along

<400> SEQUENCE: 17
cacagtttat agaccaccga cggctcatta gggctcgtca tgtaac                    46
```

```
<210> SEQ ID NO 18
<211> LENGTH: 24
<212> TYPE: DNA
<213> ORGANISM: Artificial sequence
<220> FEATURE:
<223> OTHER INFORMATION: Synthetic sequence: Probe K10F2aDab

<400> SEQUENCE: 18
gcacagttta tagaccaccg acgg                                          24

<210> SEQ ID NO 19
<211> LENGTH: 26
<212> TYPE: DNA
<213> ORGANISM: Artificial sequence
<220> FEATURE:
<223> OTHER INFORMATION: Synthetic sequence: Primer K10F1.5a

<400> SEQUENCE: 19
gctgacttca aaacgagaag agttgc                                        26
```

METHODS FOR AMPLIFYING AND DETECTING NUCLEIC ACID SEQUENCES

CROSS-REFERENCE TO RELATED APPLICATIONS

This patent application is a national stage filing under 35 U.S.C. 371 of International Application No. PCT/GB2007/003793, filed on Oct. 5, 2007, which claims foreign priority benefits to United Kingdom Patent Application No. 0619951.7, filed on Oct. 9, 2006, United Kingdom Patent Application No. 0700461.7, filed on Jan. 10, 2007, United Kingdom Patent Application No. 0702692.5, filed on Feb. 12, 2007 and United Kingdom Patent Application No. 0705029.7, filed on Mar. 15, 2007. These applications are incorporated herein by reference in their entireties.

TECHNICAL FIELD

The present invention is directed to methods and compositions for amplifying and detecting a target nucleic acid sequence in a sample, optionally in a sequence-independent manner. The methods may involve more than one primer targeting one strand of the target nucleic acid, extending the primers, strand displacement, separating complementary strands of the nucleic acid, and detecting the sequence so amplified. The invention also provides a detection system employing probes and primers, which serve as amplification primers and/or detection probes.

BACKGROUND OF THE INVENTION

This invention relates to the field of nucleic acid amplification and detection. More particularly, the invention provides methods, compositions and kits for amplifying (i.e., making multiple copies of) nucleic acid sequences and for detecting amplified sequences.

A number of target amplification methods have been developed which permit the implementation of sensitive diagnostic assays based on nucleic acid detection. They include the polymerase chain reaction (PCR) (U.S. Pat. Nos. 4,683,195 and 4,683,202), ligase chain reaction (LCR) (See, for example, Barany, Proc. Natl. Acad. Sci. USA 88:189-193 (1991)); and U.S. Pat. No. 5,494,810), self-sustained sequence replication (3SR) and nucleic acid sequence based amplification (NASBA) (See, for example, Guatelli et al., Proc. Natl. Acad. Sci. USA 87:1874-1878 (1990)). Loop-mediated isothermal amplification (LAMP) (WO 00/28082), strand displacement amplification (SDA) (See, for example, U.S. Pat. Nos. 5,455,166 and 5,470,723), Isothermal and Chimeric primer-initiated Amplification of Nucleic acids (ICAN) method described in International Publication WO02/16639, Rolling Circle Amplification (RCA) (U.S. Pat. Nos. 5,714,320 and 6,235,502), and the like.

The real-time polymerase chain reaction (PCR) is carried out in a closed-tube format and can be used to obtain quantitative results. Several methods using a labeled sequence-specific probe are currently available for performing real-time PCR, such as TaqMan® probes (U.S. Pat. Nos. 5,210,015 and 5,487,972, and Lee et al., Nucleic Acids Res. 21:3761-6, 1993); molecular beacons (U.S. Pat. Nos. 5,925,517 and 6,103,476, and Tyagi and Kramer, Nat. Biotechnol. 14:303-8, 1996); self-probing amplicons (scorpions) (U.S. Pat. No. 6,326,145, and Whitcombe et al., Nat. Biotechnol. 17:804-7, 1999); Amplisensor (Chen et al., Appl. Environ. Microbiol. 64:4210-6, 1998); Amplifluor (U.S. Pat. No. 6,117,635, and Nazarenko et al., Nucleic Acids Res. 25:2516-21, 1997 and U.S. Pat. No. 6,117,635); displacement hybridization probes (Li et al., Nucleic Acids Res. 30:E5, 2002); DzyNA-PCR (Todd et al., Clin. Chem. 46:625-30, 2000); fluorescent restriction enzyme detection (Cairns et al. Biochem. Biophys. Res. Commun. 318:684-90, 2004); and adjacent hybridization probes (U.S. Pat. No. 6,174,670 and Wittwer et al., Biotechniques 22:130-1, 134-8, 1997).

Strand displacement reaction has been implemented in a number of amplification methods. These methods include SDA, LAMP, ICAN, RCA, and the like. RCA has been further developed in a technique, named Multiple Displacement Amplification (MDA), which generates a whole genome amplification (See, for example, U.S. Pat. No. 6,124,120 and Dean et. al., Proc. Natl. Acad. Sci. USA 99:5261-5266 (2002)). Another method named isothermal strand displacement nucleic acid amplification has been developed (see U.S. Pat. Nos. RE38,960E, RE39,007E). These methods use strand displacement, multiple primers and isothermal conditions to achieve a substantial amplification. However, these methods suffer from a number of drawbacks such as difficulty of quantification, slow reaction, non-specific spurious product, low sensitivity etc.

PCR remains the most widely used DNA amplification and quantitation method. Nested PCR, a two-stage PCR, is used to increase the specificity and sensitivity of the PCR (U.S. Pat. No. 4,683,195). Nested primers for use in the PCR amplification are oligonucleotides having sequence complementary to a region on a target sequence between reverse and forward primer targeting sites. However, PCR in general has several limitations. PCR amplification can only achieve less than two fold increase of the amount of target sequence at each cycle. It is still relatively slow. The sensitivity of this method is typically limited, making it difficult to detect target that may be present at only a few molecules in a single reaction.

Current technologies for generating single stranded amplification end product include PCR based methods such as asymmetric PCR (Gyllensten et al., Proc. Natl. Acad. Sci. USA 85:7652-7656, 1988), LATE-PCR (Sanchez et al., Proc. Natl. Acad. Sci. USA 101:1933-1938, 2004), and a method described in BioTechniques, 40:759-763, 2006 by Tang et al. A non-PCR based method called polynomial amplification of nucleic acids has been developed (U.S. Pat. No. 7,112,406). Due to the non-exponential nature of amplification, the polynomial amplification could reduce levels of carry-over contamination. However this is at the expense of amplification efficiency. Overall, all these methods are inefficient and the generated single stranded amplification end product is not suitable for monitoring the amplification process and is not suitable for real-time detecting and quantification of amount of target present in a sample.

Thus it can be seen that novel methods and materials addressing one or more of these drawbacks would provide a contribution to the art.

DISCLOSURE OF THE INVENTION

The present invention, in different aspects and embodiments, provides nucleic acid amplification and detection methods that are both sensitive and fast. In embodiments described below, amplification methods employing exponential amplification and strand displacement are provided which achieve more than two fold increase of the amount of a target nucleic acid sequence at each cycle.

The invention further provides an amplification system that can efficiently generate single-stranded end products that may find various uses, for example for real-time detecting, for generating probes for hybridization for microarrays or FISH etc.

Thus in preferred embodiments the system of the present invention provides methods for amplifying a target which is sensitive, selective and generates single stranded detection products in an efficient format.

The present invention provides for amplification and detection of target nucleic acid by multiple primer extension, strand displacement, separating double stranded nucleic acid, and repeating the above steps. In one aspect, there is provided a method for amplifying a target nucleic acid sequence of interest in a sample, wherein said target nucleic acid comprises one strand, for example single-stranded RNA or two separate complementary strands, for example denatured genomic DNA, the method comprising the steps of:

(a) treating the sample with at least two oligonucleotide primers capable of hybridizing to the or one strand of said target sequence (which may be termed herein a "first strand") and at least one oligonucleotide primer capable of hybridizing to the complementary strand of said target sequence (which may be termed herein a "second" strand) wherein said treating is carried out under hybridizing and extension conditions such that an extension product of each primer will be synthesized complementary to its hybridizing strand of the target sequence;

wherein said at least two primers for one strand of the target sequence comprises one outer primer and one or more inner primers, which hybridize to the target sequence in 5' to 3' order In one embodiment one or more of said primers is a linker-primer which comprises a linker. The linker plays a role so that a single-stranded end product is generated. In different embodiments the linker may take different forms:

First, the linker may be a blocking moiety, wherein the replication of all or part of said linker-primer is blocked, whereby the primer extension molecule generated from a template of the linker-primer extension strand is not suitable as a template for a further primer extension as it lacks a primer binding site. The blocking moiety may be selected from the group consisting of a hydrocarbon arm, non-nucleotide compound, HEG, nucleotides derivatives, 5'-nitroindole, 1,3-propanediol, an abasic ribose or a dye. The blocking moiety may be located at less than 18 nucleotides away from 3' terminus of the linker-primer. It is preferred that the blocking moiety may be located at less than 6 nucleotides away from 3' terminus of the linker-primer. It is more preferred that the blocking moiety may be located at less than 3 nucleotides away from 3' terminus of the linker-primer. Herein this type of linker is called as "linker blocking moiety".

Second, the linker-primer may comprise a 3' target complementary portion (which may be termed herein a "priming portion") capable of priming extension upon hybridizing to said target sequence and 5' thereto a "linker sequence" (which may be a sequence of nucleotides or non-nucleic acid) which comprises a sequence complementary or substantially complementary to a part of the target sequence or target derived sequence. Herein this type of linker is called as "linker sequence". The target derived sequence may be the linker-primer extension product.

Third, the linker-primer may comprise cleavable moieties (also referred to as cleavable linkers). Thus, the linker-primer is a cleavable primer, which is cleaved on the cleavable moieties or degraded completely or partially by an enzymatic agent when said cleavable primer forms a hybrid with its complementary nucleic acid sequence, wherein the enzymatic agent comprises a RNase H activity when said linker-primer is an RNA-type primer made of ribonucleotides and/or modified ribonucleotide. The cleavable linker-primer may comprise at lease 60% ribonucleotides and/or modified ribonucleotide, wherein other nucleotides selected from the group consisting of a deoxyribonucleotide and a nucleotide analog are positioned evenly or in clusters among the ribonucleotides. Alternatively, the cleavable linker-primer may comprise at lease 30% ribonucleotides and/or modified ribonucleotide, wherein other nucleotides selected from the group consisting of a deoxyribonucleotide and a nucleotide analog are positioned evenly or in clusters among the ribonucleotides. Or the cleavable linker-primer may comprise at least 10% ribonucleotides and/or modified ribonucleotide, wherein other nucleotides selected from the group consisting of a deoxyribonucleotide and a nucleotide analog are positioned evenly or in clusters among the ribonucleotides;

and permitting hybridizing and extension of said primers to be repeated at least once;

(b) separating the primer extension products from templates to produce single-stranded molecules;

(c) treating the single-stranded molecules generated from step (b) with the primers of step (a) under hybridizing and extension conditions such that a primer extension product is synthesized using the single-stranded molecules produced in step (b) as a template, wherein said hybridization condition and extension condition are repeated at least once; and (d) repeating steps (b) and (c) at least once; whereby said target nucleic acid sequence may be detected by detecting the primer extension products especially the single-stranded end product.

In the embodiments of the present invention, the amplification of target nucleic acid is exponential and more than two-fold increase of amplification product at each cycle may be achieved, wherein the outer primer is not a linker-primer (i.e. is replicable).

It will be understood that the terms 'first' and 'second' are used relatively herein to denote the binding of the primer pairs. Thus either or both strands may, for the purposes of the invention, be termed a "first" or "second" strand, with respect to any recited primer.

It will be further understood that 'in 5' to 3' order' refers to the relative position of the primers on the template strand.

Thus an amplification method of the invention as set out above may further comprise detecting said single stranded end product. The linker-primer will preferably be employed in which the "linker blocking moiety" blocks the replication of all or part of the linker-primer sequence or the cleavable linker-primer is degraded partially or completely when it forms a hybrid with its complementary nucleic acid or the linker sequence is complementary to a part of the target sequence on its extension strand. In one embodiment, a single stranded end product is generated because the "linker blocking moiety" prevents a primer extending beyond the blocking moiety on the template of the linker-primer extension molecule or the linker-primer sequence on the linker-primer extension molecule is cleaved. In another embodiment, a linker-primer will be employed in which the linker sequence represents a sequence complementary to the linker-primer extension strand. The linker-primer extension product, or its complementary strand, or a primer extension product generated from using the extended complememtary strand of the linker-primer extension product, upon becoming single stranded, folds to form a stem-loop structure under hybridizing conditions. Herein the product with stem-loop structure is also referred to as "single-stranded end product". The hybridization between a probe and the single-stranded end product may be detected via a detectable change in a detection system.

In one aspect a detection system is provided for detecting a target nucleic acid sequence in a sample. Such system comprises primers and detection probes, wherein said primer is a linker-primer which comprises a 5' linker sequence, wherein said linker sequence is complementary to a part of target sequence or target derived sequence. The linker-primer comprises 5' additional sequence and/or 3' additional sequence flanking the linker sequence, wherein one or two of said probes comprise sequences complementary to said additional sequences of the linker-primer, wherein one or two of said probes comprise sequences complementary to a part (s) of target sequence or target derived sequence. Upon hybridization the double stranded stem structure formed by linker sequence and target sequence brings two or more detection labels of the probes into close or substantially close proximity (FIGS. 3A, B, E, F, J, K, L, M and N).

It is appreciated that in the above detection system the linker-primer may simply function as probe. The linker sequence of some of linker-primers that are in excess amount in a reaction and are not incorporated into a primer extension product may hybridize to a target sequence and bring detection labels into close proximity, therefore generating detection signals. In this case, the 3' target complementary portion of the linker primer is not needed and 3' end of it may be blocked (FIGS. 3L and M).

In another aspect, the double stranded stem region formed by hybridizing the linker portion to the linker-primer extension strand may comprise a primer binding site, therefore preventing or inhibiting a corresponding primer annealing, and the loop portion may lack other primer binding sites, it will be appreciated that this will lead to accumulation of the single stranded linker-primer extension product.

It will further be appreciated that the DNA polymerase employed will be a DNA polymerase with strand displacement activity, preferably lacking 5' to 3' exonuclease activity, e.g. Vent(exo-) and Tfu polymerases, or a strand displacement factor will be employed.

In the amplification method of the invention as discussed above, the linker-primer may be substituted by a primer without a linker. In another aspect, the invention thus provides a method for amplifying a target nucleic acid sequence of interest in a sample, wherein said amplifying achieves more than two fold increase of the amount of said target nucleic acid sequence at each cycle, the method comprising the steps of: (a) treating the sample with at least two forward primers for one strand of the target sequence and at least one reverse primer for the complementary strand of the target sequence, under hybridizing conditions and extension conditions such that an extension product of each primer is synthesized which is complementary to its hybridizing nucleic acid strand, wherein said hybridizing condition and extension condition are repeated at least once, wherein said extension condition permits primer extension and strand displacement activity; (b) separating (denaturing) the primer extension products to produce single-stranded molecules; (c) treating the single-stranded molecules generated from step (b) with the primers of step (a) under hybridizing and extension conditions such that a primer extension product is synthesized using the single stranded molecules produced in step (b) as a template, wherein said hybridizing condition and extension condition are repeated at least once, wherein said extension condition permits primer extension and strand displacement activity; and (d) repeating steps (b) and (c) at least once. Such an amplification method may further comprise detection of amplified target sequence.

In another aspect, the invention provides a method for amplifying any stretch of nucleic acid in a sequence-independent manner, the method comprising the steps of: (a) treating the sample with a degenerate primer (which may consist of a plurality of random oligonucleotide primers), under hybridizing condition such that the primer hybridizes to many places of said nucleic acid to allow the formation of a nucleic acid-primer hybrid and under extension condition such that primer extension products are synthesized, wherein said degenerate primer comprises random or partially random nucleotides, wherein said hybridizing condition and extension condition are repeated at least once, wherein said extension condition permits primer extension and strand displacement activity; (b) separating (denaturing) the primer extension products to produce single-stranded molecules; (c) treating the single-stranded molecules generated from step (b) with the primers of step (a) under hybridizing and extension conditions such that primer extension products are synthesized using the single stranded molecules produced in step (b) as a template, wherein said hybridizing condition and extension condition are repeated at least once, wherein said extension condition permits primer extension and strand displacement activity; and (d) repeating steps (b) and (c) at least once. In one embodiment, the degenerate primer comprises a non-random portion 5' of the random or partially random nucleotides, wherein the amplification reaction comprises said degenerate primer and a universal primer, wherein said universal primer comprises said non random portion sequence of the degenerate primer. Preferably this non-random sequence will be one which it is believed is not present in the target.

BRIEF DESCRIPTION OF THE FIGURES

In FIG. 2A, the linker primer F2 comprises a blocking moiety. In other figures, the linker-primer F2 contains a 5' linker sequence which is complementary to a part of sequence in the F2 extension strand 2B, or identical to the sequence of primer R1(2C, 2D), or identical to the sequence of primer R2(2E). Under hybridizing condition each primer anneals to each strand of the target sequence. Under extension condition an extension product of each primer is synthesized which is complementary to each nucleic acid strand. The linker-primer F2 extension product is displaced by primer F1 extension reaction. In the case of (2A), F2 primer extension strand acts as template to synthesize the R1 primer extension product, whereas the R1 primer extension product generated on the template of F2 primer extension strand cannot act as a template for a further primer extension, whereby accumulating the single-stranded R1 primer extension product. In the cases of (2B, 2C, 2D and 2E), the strand-displaced linker-primer extension product tends to fold and form a stem-loop structure as this folding is kinetically favored. The double stranded stem portion comprises the binding site for R1 which prevents or inhibits primer R1 annealing, thereby accumulating the single stranded product (2C). However, the linker-primer F2 extension product may comprise other primer binding sites which are not blocked (2B, 2D, 2E), thereby further extension and strand displacement can occur. In (2E), R1 primer extension molecule generated on the template of the linker-primer extension molecule folds to form a stem-loop structure (herein terms "the first R1 primer extension molecule"), wherein the 3' end of the first R1 primer extension molecule anneals to itself and primes an extension. At the same time, the linker-primer anneals to the first R1 primer extension molecule and primes an extension which subsequently displaces the strand generated from the 3' end of the first R1 primer extension molecule, thereby opening up the stem-loop structure. Upon opening up the stem-loop structure of the first R1 primer extension molecule, the R1 primer anneals to 3' end of the extended first R1 primer extension molecule and initiates to synthesize a second R1 primer extension molecule, which displaces the linker-primer extension strand. The displaced linker-primer extension strand acts as a template for a further primer extension. The second R1 primer extension molecule, upon subjecting to denaturing and hybridizing conditions, folds to form a stem-loop structure which does not contain an available primer binding site, whereby the reaction is accumulating this structure and the loop part is suitable for a probe binding in a detection system. The double stranded molecules formed by the primer extension reaction are denatured. The denatured molecules are treated with the same primers above under hybridizing and extension conditions such that primer extension products are synthesized. The hybridizing and extension conditions are repeated at least once. Then the steps, denaturing and the repeated hybridizing and extension conditions, are repeated at least once. The FIG. 2F illustrates a loop-mediated isothermal amplification utilising a linker-primer having a blocking moiety to generate a single-stranded end product.

DETAILED DESCRIPTION OF THE INVENTION

Figure 1:
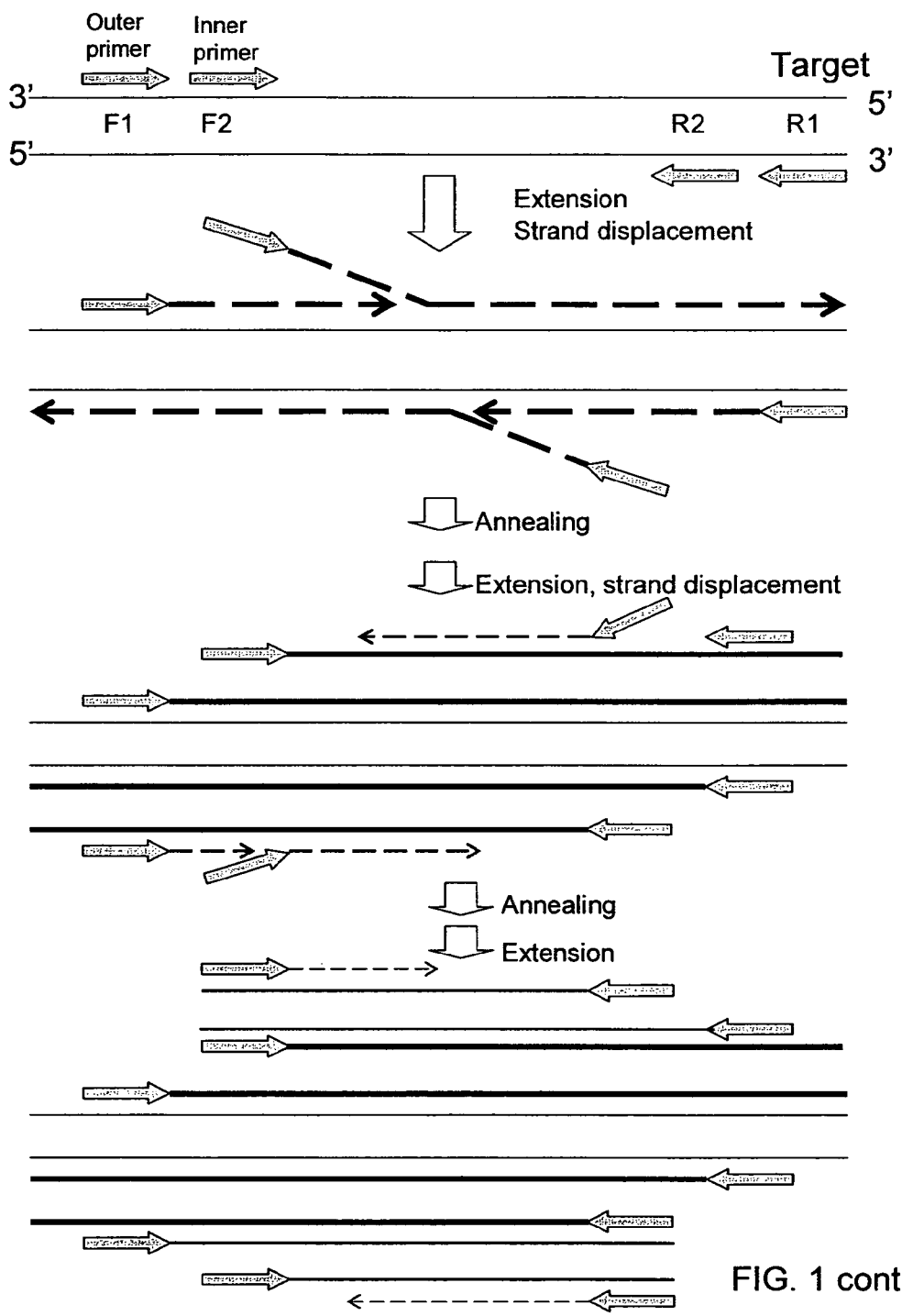
FIG. 1 provides an illustration of the steps and products of an amplifying method. A target nucleic acid sample comprising two separate complementary strands is mixed with two forward primers, outer primer F1 and inner primer F2, and two reverse primers, outer primer R1 and inner primer R2. Under hybridizing condition each primer anneals to each strand of the target sequence. Under extension condition an extension product of each primer is synthesized which is complementary to each nucleic acid strand. The inner primer extension product is displaced by outer primer extension reaction. The strand displaced inner primer extension product is again subjected to hybridizing condition and extension condition, which are repeated at least once. The primer extended strand is separated from template, which may be carried out by denaturing. The denaturizing is normally carried out by heating. The denatured single stranded molecules are treated with the same primers above under hybridizing and extension conditions such that primer extension products are synthesized. The hybridizing condition (for example 58° C.) and extension condition (for example 72° C.) are repeated at least once. Then the steps, denaturing and the repeated hybridizing and extension conditions, are repeated at least once.
Figure 1:
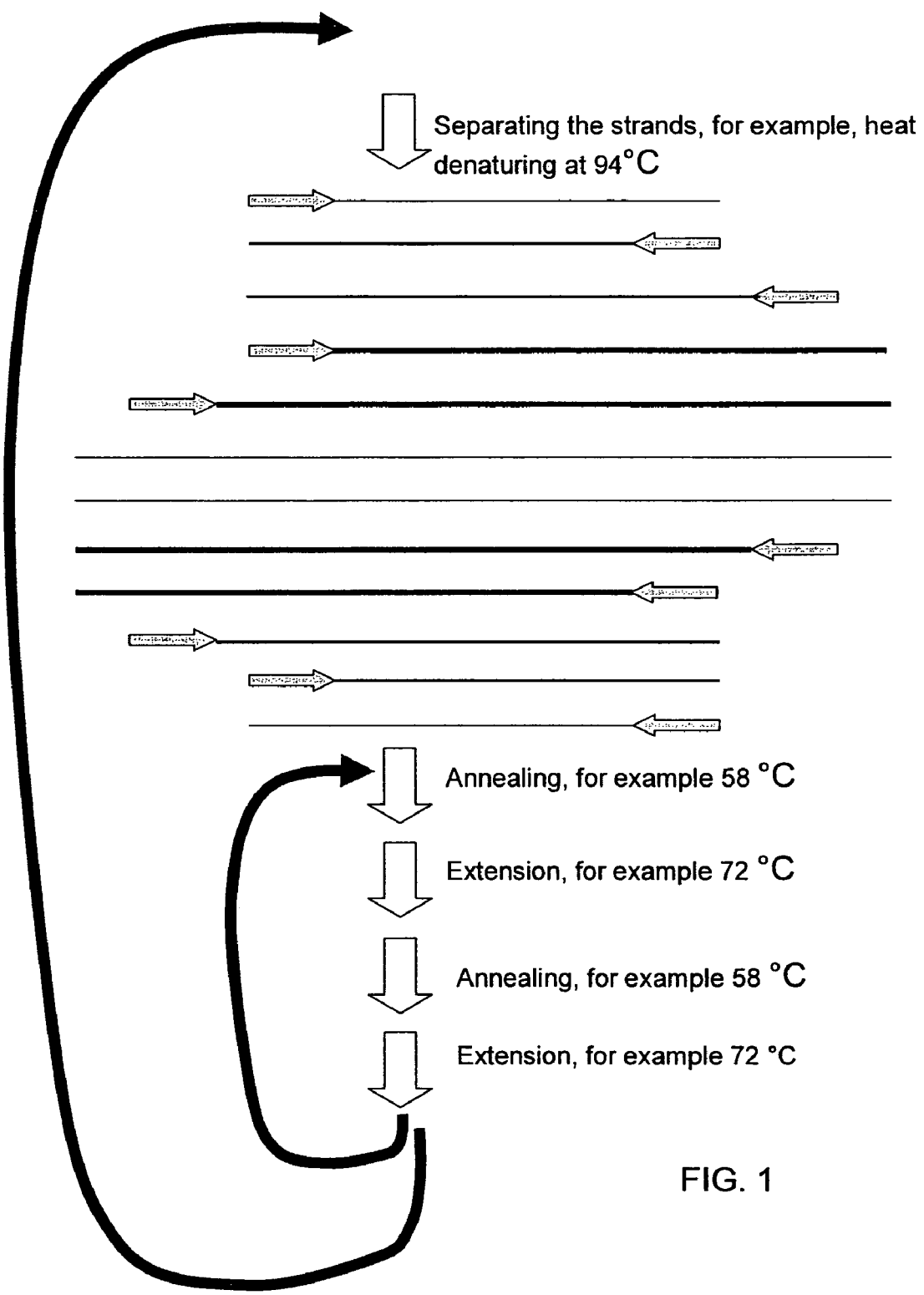

The present invention is directed to a method for amplifying and detecting any one or more desired specific nucleic acid sequences found in a sample. Because large amounts of specific sequence can be produced by this method, the present invention may be used for amplifying and detecting a target sequence efficiently.

I. Materials

A. Target Sequences

The target sequence, which is the object of amplification and detection, can be any nucleic acid. The target sequence can be RNA, cDNA, genomic DNA, DNA from a disease-causing microorganism or virus. The target sequence can also be DNA treated by chemical reagents, various enzymes and physical exposure. A target nucleic acid sequence of interest in a sample may appear as single stranded DNA or RNA such as cDNA, mRNA, other RNA, or as separated complementary strands. Separating complementary strands of target nucleic acid may be accomplished by physical, chemical or enzymatic means.

B. Primers

The term "Primer" as used herein refers to an oligonucleotide, whether occurring naturally or produced synthetically, which is capable of acting as a point of initiation of synthesis when placed under conditions in which synthesis of primer extension product which is complementary to a nucleic acid strand is induced i.e., in the presence of nucleotides and an agent for polymerization such as DNA polymerase and at a suitable temperature and buffer. The primer is preferably single stranded for maximum efficiency in amplification, but may alternatively be double stranded. The primer must be sufficiently long to prime the synthesis of extension products in the presence of the inducing agent. The exact lengths of the primers will depend on many factors, including temperature, source of primer and use of the method.

The primers herein are selected to be substantially complementary to the different strands of each specific sequence to be amplified. This means that the primers must be sufficiently complementary to hybridize with their respective strands. Therefore, the primer sequence need not reflect the exact sequence of the template. A primer sufficiently complementary to hybridize with its respective strand is often referred to as the primer for the strand of the target sequence in this specification.

Primers for use in the disclosed methods are oligonucleotides comprising 3' sequences complementary to target sequences, which is normally used for priming an extension reaction. This part of primer is referred to as the 3' target complementary portion or priming portion. The 3' target complementary portion of a primer can be any length that supports specific and stable hybridization between the primer and target sequence. Generally this is 9 to 40 nucleotides long, but is preferably 15 to 25 nucleotides long.

A target nucleic acid sequence of interest in a sample may comprise one strand, for example single stranded RNA, first strand cDNA or two separate complementary strands, for example denatured genomic DNA. At least two forward oligonucleotide primers are required for annealing to one strand of the target sequence. For exponential amplification, apart from at least two forward primers, at least one reverse oligonucleotide primer is required for annealing to the complementary strand of the target sequence. The two oligonucleotide primers that hybridize to the same strand of target sequence are referred herein as a outer primer and a inner primer, which hybridize to target sequence in 5' to 3' order. There may be more than one inner primer that is capable of hybridizing to a region of the target which lies 3' relative to the sequence or region to which the outer primer hybridizes or possesses substantial base complementarities, and that is preferred. For the complementary strand of the target sequence, there may be no inner primer, but provision of one or more inner primer is preferred.

Primers may comprise additional sequences at the 5' ends of primers that are not complementary to target sequences. This sequence is referred to as the 5' non-complementary portion. The 5' non-complementary, portion of a primer comprises sequence elements that are useful for various embodiments of the invention. Firstly, common restriction sites can be incorporated into the non-complementary portions of selected primers and are used for digesting nucleic acid fragments amplified. Secondly, unique sequences or specific restriction sites in the 5' non-complementary portions can serve as detection markers for distinguishing different alleles, different genes or any targets of interest. Thirdly, the 5' non-complementary portion of primers can facilitate extension, amplification, and especially the strand displacement reaction.

In one embodiment one or more of said primers is a linker-primer which comprises a linker. The linker plays a role so that a single stranded end product is generated.

Figure 2A:
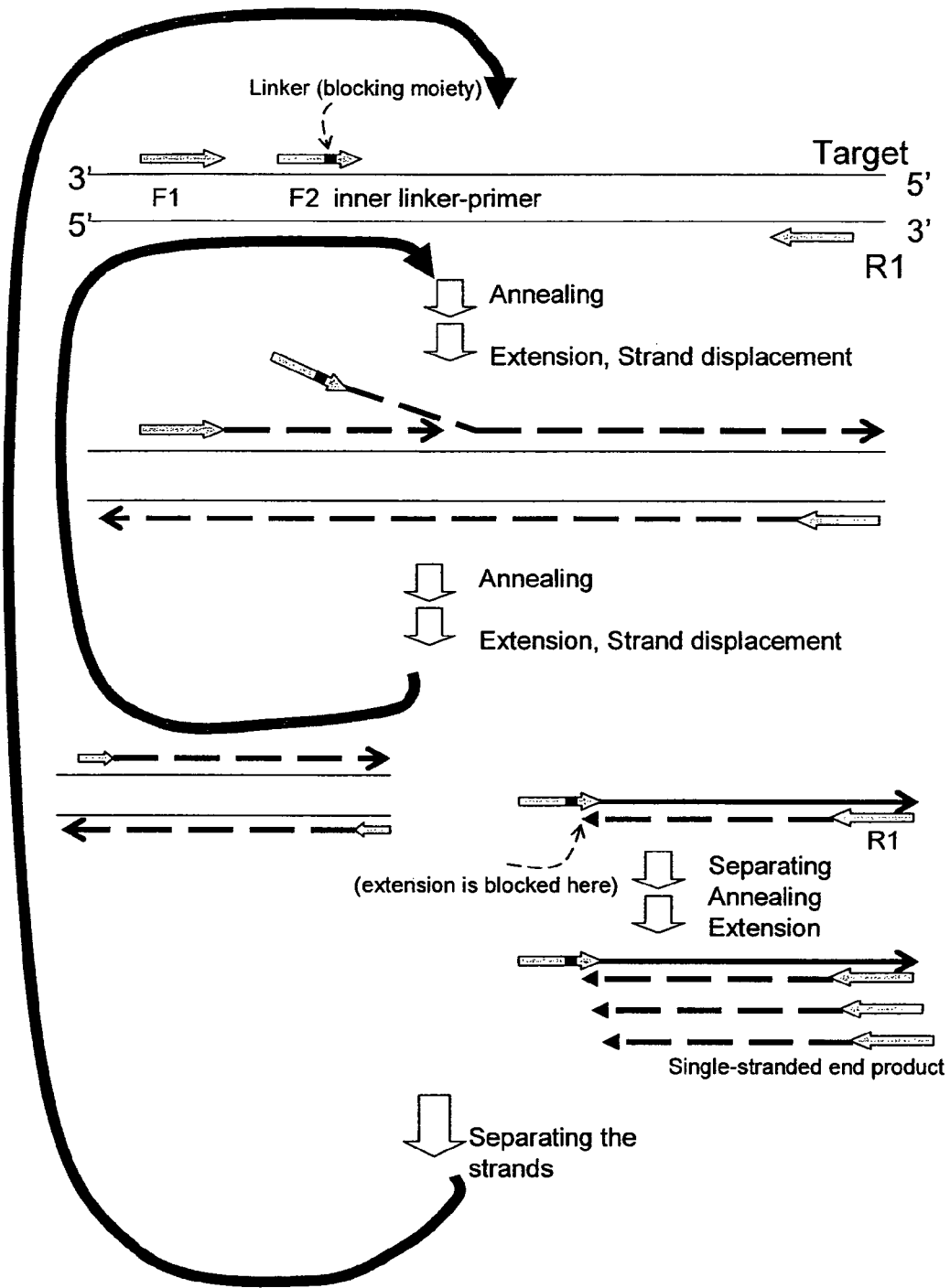
FIGS. 2A to 2E illustrate methods using linker-primers. A target nucleic acid sample comprising two separate complementary strands is mixed with two forward primers, outer primer F1 and inner primer F2, and one or two reverse primer R1 and R2.

First, the linker may be a blocking moiety, wherein the replication of all or part of said linker-primer is blocked (FIG. 2A), whereby the primer extension molecule generated on the template of the linker-primer extension strand is not suitable as a template for a further primer extension as it lacks a primer binding site. "Blocking moiety" refers to an agent capable of blocking the replication of a nucleic acid template by a nucleic acid polymerase (DNA polymerase, RNA polymerase, reverse transcriptase or replicase). Such agents are known. A blocking moiety may be a nucleic compound (for example a modified nucleotide), or a non-nucleic compound, which is not recognized as a template by the relevant polymerase. The blocking agent may be a hydrocarbon arm inserted between two nucleotides of the nucleic template at the site where it is desired to stop the replication. The expression "hydrocarbon arm" means here "essentially hydrocarbon arm": It is for example a polymethylene arm which may be inserted between two nucleotides, for example by the reaction of a diol or of a diamine (see the experimental section below). Such a polymethylene group may contain substituents or may be interrupted by one or more oxygen, sulphur or nitrogen heteroatoms for example. In principle, the blocking moiety included in the linker-primer may be any entity which is not recognized as suitable template by a polymerase. It is desirable that the blocking moiety is capable of insertion in synthetic oligonucleotides by incorporation of appropriate precursors (e.g. phosphoramidites) during in vitro synthesis of the oligonucleotide. A particular blocking moiety is a hexethylene glycol (HEG) monomer. Other groups such as alkyl groups, non-nucleotide linkers, phosphorothioate, alkane-diol residues, peptide nucleic acid, nucleotide derivatives or a dye can be used. The blocking moiety may be located at less than 18 nucleotides away from 3' terminus of the linker-primer. It is preferred that the blocking moiety may be located at less than 6 nucleotides away from 3' terminus of the linker-primer. It is more preferred that the blocking moiety may be located at less than 3 nucleotides away from 3' terminus of the linker-primer.

Figure 2B:
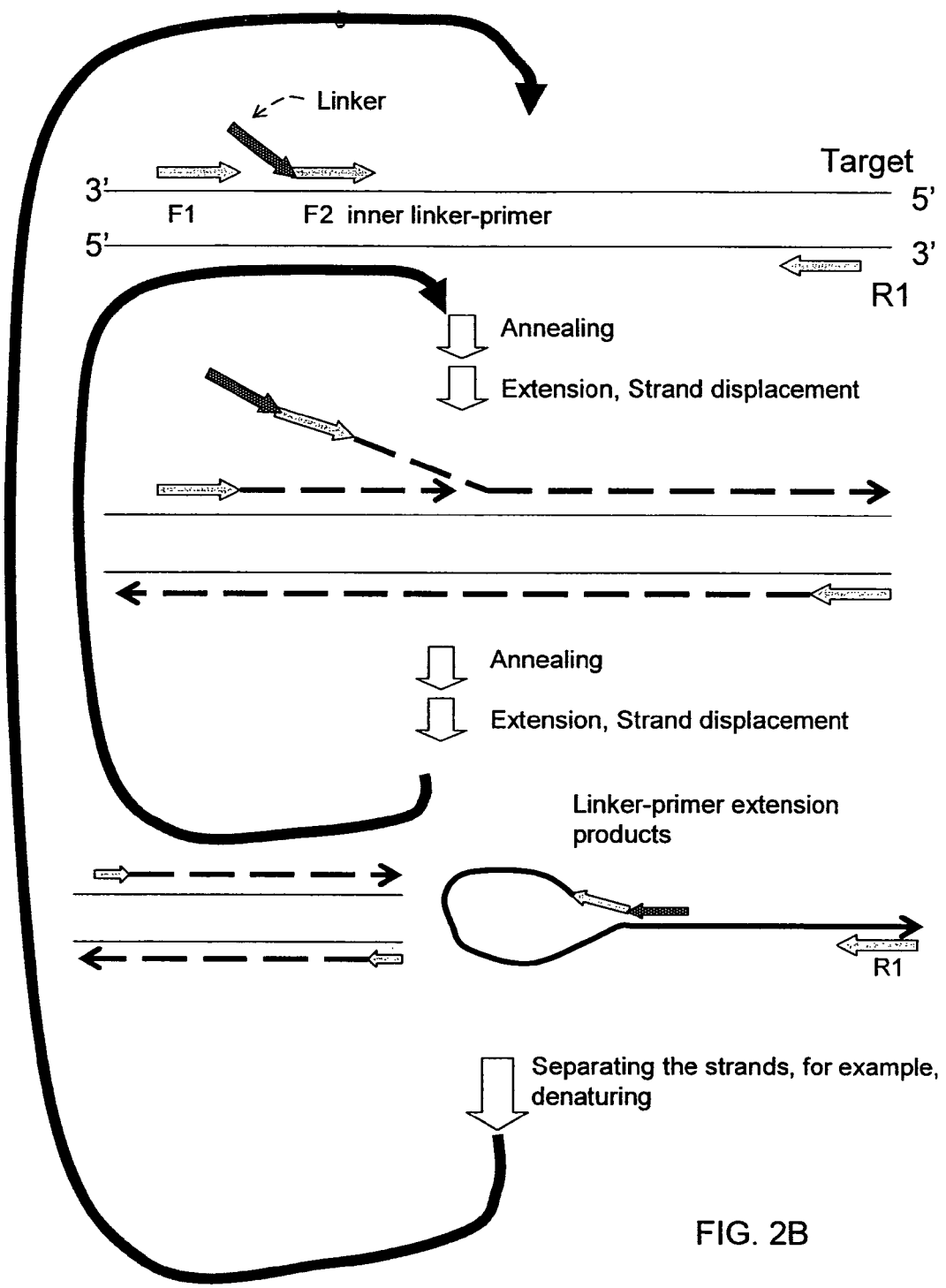

Second, the linker-primer may comprise a 3' target complementary portion (priming portion), which may or may not be interrupted by a blocking moiety, capable of priming extension upon hybridizing to said target sequence and 5' thereto a "linker sequence" (which may be a sequence of nucleotides or non-nucleic acid) which will hybridize to a part of the target sequence or target derived sequence. The target derived sequence may be the linker-primer extension product (FIG. 2B)

Figure 2C:
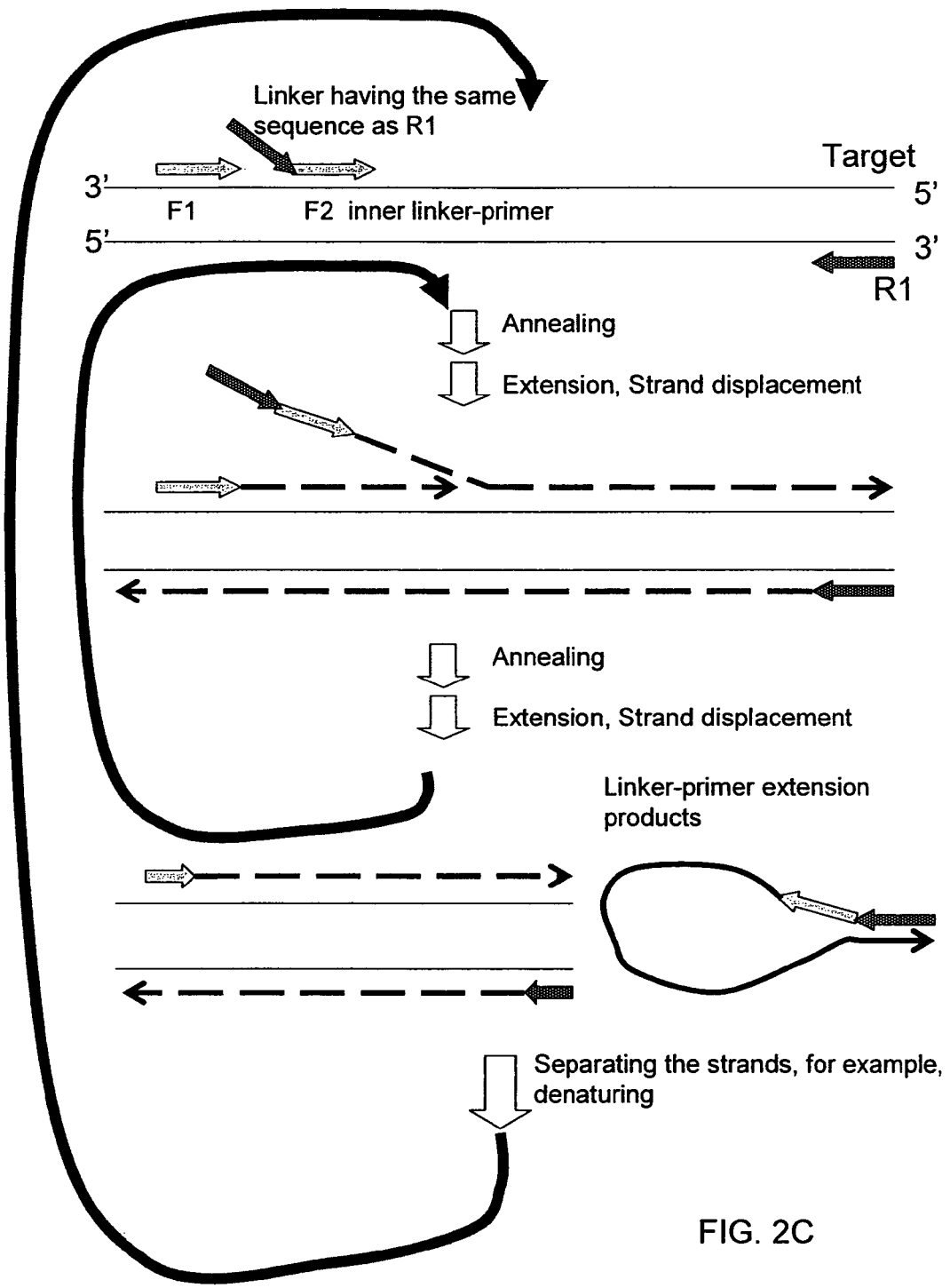
Figure 2D:
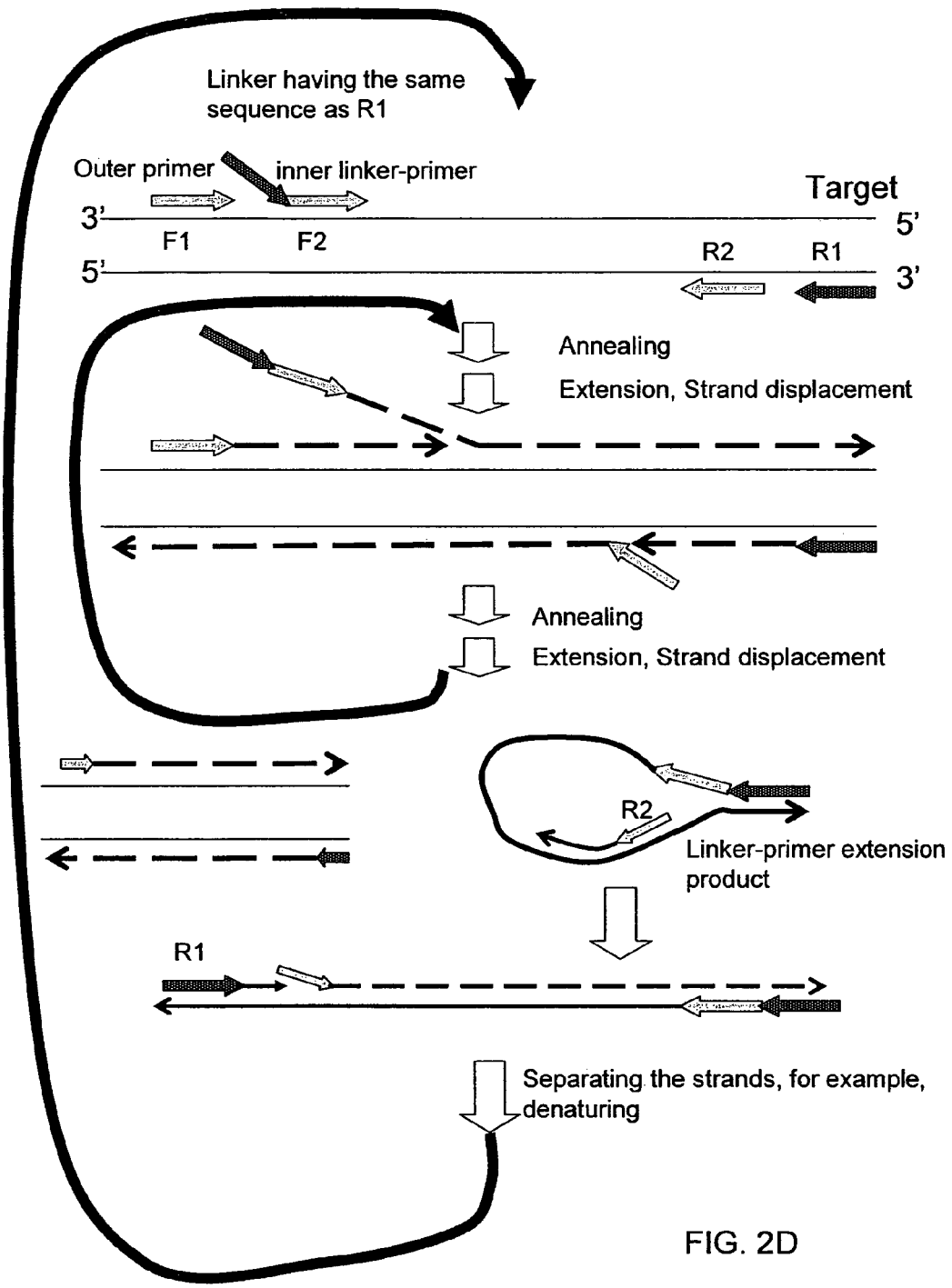
Figure 2E:
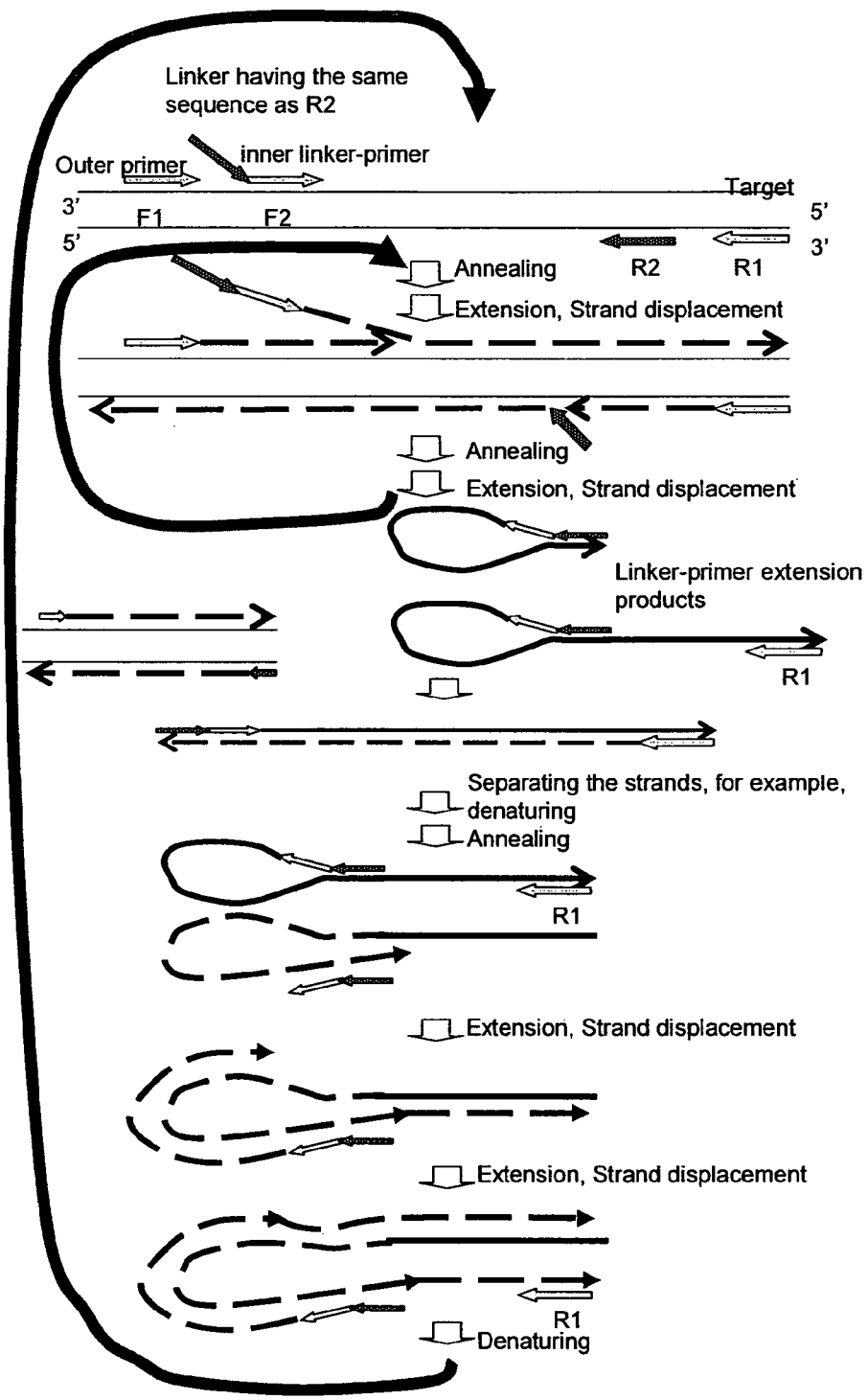
Figure 2F:
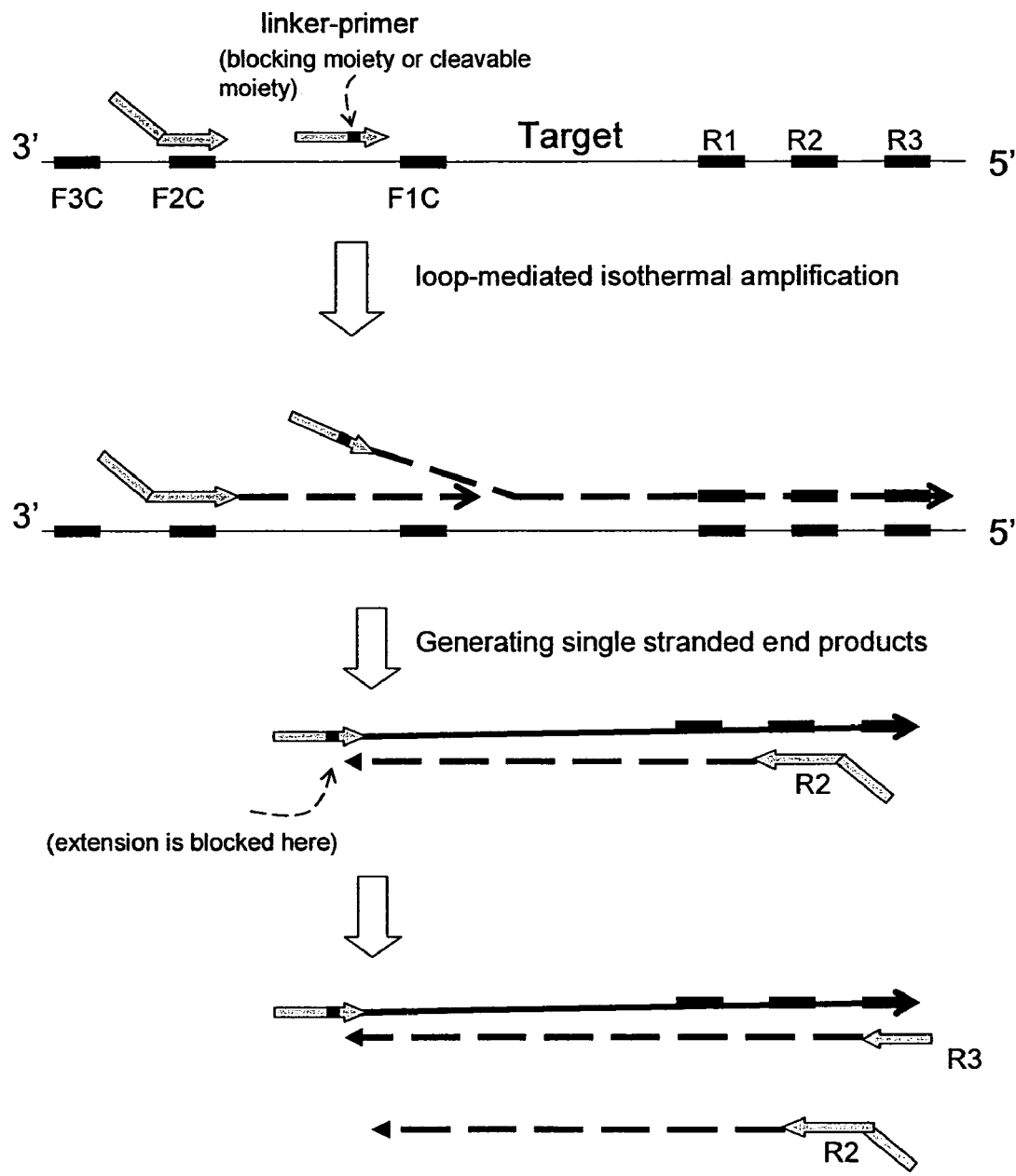
FIG. 2G illustrates a method using a cleavable linker-primer, which may be a RNA-type primer.

In one embodiment, the linker sequence is identical or substantially identical to the sequence of one of other primers (FIG. 2C, 2D, 2E). It is preferred that the linker sequence in a linker-primer is identical or substantially identical to the sequence of one of the primers for the complementary strand of the target sequence. In a preferred embodiment, the linker sequence is identical or substantially identical to the 3' target complementary portion of one of the primers for the complementary strand of the target sequence. In other words, the linker sequence of a forward primer has the same or similar sequence as one of reverse primers. Examples of the use of such a linker-primer are illustrated in FIG. 2. In a preferred embodiment, if there is more than one reverse primer, the linker sequence of an inner forward primer has the same or similar sequence as one of inner reverse primers. The linker-primer may comprise 5' additional sequence (portion) or/and 3' additional sequence (portion) flanking the linker sequence that may be not identical or not complementary to any part of the target sequence (FIG. 3). The additional sequence may support a detection and/or amplification process. The 5' or 3' additional sequence may hybridize to a detection probe. For this purpose, the additional sequence flanking the linker sequence can comprise any nucleotides and can be any length. The hybridizations between probe and linker-primer and between linker and target are detected via a detectable change of detection labels.

Third, the linker-primer may comprise cleavable moieties (also referred to as cleavable linkers). Thus, the linker-primer is a cleavable primer, which is cleaved on the cleavable moieties or degraded completely or partially by an enzymatic agent when said cleavable primer forms a hybrid with its complementary nucleic acid sequence. Cleavable moieties may include a restriction enzyme site, or a nicking enzyme site, wherein the enzymatic agent is a restriction enzyme or nicking enzyme. It is preferred that the cleavable moiety is ribonucleotide. In this case, the linker-primer is RNA-type primer comprising ribonucleotides.

As used herein, a ribonucleotide may be an unmodified ribonucleotide and/or a modified ribonucleotide that is recognized by or cleaved with an endonuclease, which may be RNase H. The ribonucleotides include both unmodified ribonucleotide and modified ribonucleotide as described above. An unmodified ribonucleotide, a modified ribonucleotide or a combination thereof can be used for the cleavable linker-primer of the present invention as long as it does not abolish the function of the primer. Examples of the modified ribonucleotides include, but are not limited to, an (.alpha.-S) ribonucleotide in which the oxygen atom bound to the phosphate group is replaced by a sulfur atom, and a ribonucleotide in which the hydroxy group at the 2-position of the ribose is replaced by a methoxy group. Such a primer containing a modified ribonucleotide can be produced by using, for example, an (.alpha.-S) ribonucleotide triphosphate, which is prepared by a method using a sulfuration reaction reagent (Glen Research) as described in U.S. Pat. No. 5,003,097, or a 2-OMe. It is preferred that a modified ribonucleotide included in a linker-primer may be LNA (locked nucleic acid) which contains a methylene 2'-O, 4'-C linkage. This bridge reduces the conformational flexibility and confers a RNA-like C3'-endo conformation to the sugar moiety of the nucleotide.

In one embodiment, the cleavable linker-primer comprises 100% of ribonucleotides and/or modified ribonucleotides. In other embodiments, the cleavable linker-primer is a chimeric primer comprising at least one non-ribonucleotide. The cleavable linker-primer may comprise at lease 60% ribonucleotides and/or modified ribonucleotide, wherein other nucleotides selected from the group consisting of a deoxyribonucleotide and a nucleotide analog are positioned evenly or in clusters among the ribonucleotides. Alternatively, the cleavable linker-primer may comprise at lease 30% ribonucleotides and/or modified ribonucleotide, wherein other nucleotides selected from the group consisting of a deoxyribonucleotide and a nucleotide analog are positioned evenly or in clusters among the ribonucleotides. Or the cleavable linker-primer may comprise at lease 10% ribonucleotides and/or modified ribonucleotide, wherein other nucleotides selected from the group consisting of a deoxyribonucleotide and a nucleotide analog are positioned evenly or in clusters among the ribonucleotides.

The cleavable linker-primer used according to the present invention has a structure in which a nuclease recognizes and cleaves a part or whole of the linker primer sequence from a DNA strand extended from the linker primer by the action of a DNA polymerase (a primer-extended strand) at a site that contains cleavable moieties such as one or more ribonucleotides. Although it is not intended to limit the present invention, for example, when an RNase H acts on a double-stranded nucleic acid generated by extending a DNA strand from a linker-primer that has been annealed to a nucleic acid as a template, the linker-primer is cleaved at the ribonucleotide portion. Since the linker-primer sequence is degraded from the double-stranded nucleic acid which is generated by the extension of the linker primer, a new linker-primer may anneal to the previous linker-primer binding site, and initiate a new primer extension and strand displacement. Thus, any cleavable linker-primer that can be used to extend a nucleic acid strand from the 3' terminus of the primer, that can be cleaved with a nuclease, and with which a DNA polymerase can effect a strand displacement reaction, can be used in the method of the present invention.

It should be appreciated that a linker-primer may comprise any combination of the above three types of linkers.

For an exponential amplification, the outer primers may not be linker-primers. The two outer primers, one capable of priming extension on one strand of the target sequence, and another one capable of priming extension on second strand of the target sequence, may be ordinary amplification primers similar as used for PCR amplification. However it will be appreciated that the methods of the present invention differ from basic PCR, inter alia, because there is more than one primer capable of hybridising to one strand of nucleic acid template and priming extension simultaneously, and strand displacement is employed so that the extension from the outer primer displaces the extension strand of the inner primer. A more than two-fold increase of amplification product, in addition to concomitant production of single stranded product, may be achieved.

In another embodiment of the invention, in a method for amplifying any stretch of nucleic acid in a sample, a degenerate primer (a plurality of random oligonucleotide primers) having random or partially random nucleotide sequences is used. In particular, the random or partially random nucleotide sequences are located at 3' end of the degenerate primer that is the 3' priming portion of the primer. The number of random base position in the 3' end of primer can be any percentage of total number of nucleotides in the 3' end of primer. In general, from 10% to 100% is preferred, and from 50% to 100% is most preferred. The random sequence region may comprise sequence with all possible nucleotide combination, which will be sufficiently long to provide for efficient hybridization to the random place of target sequence, where the region will typically range in length from 3 to 25 nucleotides in length, usually 4 to 20 nucleotides in length, and more usually from 5 to 15 nucleotides in length. The degenerate primer may comprise a non-random portion 5' of the random or partially random nucleotides. The 5' non-random portion sequence may comprise any sequence. In general, the sequence of this region can be chosen such that it is not significantly similar to the target sequence. The length of the 5' non-random portion sequence will range from 14 to 60, usually from about 18 to 40 and more usually from about 20 to 30 nucleotides in length. In another embodiment, the amplification reaction comprises a degenerate primer and a universal primer. The degenerate primer comprises random or partially random nucleotides at its 3' end and a universal non-random portion sequence 5' of the random or partially random nucleotides, while the universal primer comprises the non-random portion sequence of the degenerate primer.

A non-limiting 'degenerate primer' as used herein may have the sequence:

```
                                              (SEQ ID NO: 1)
GTGTAGCGTGAAGACGACAGAAAGGGCGNNNNNNNNNNTWTR (where R is G or A; W is A or T)
```

The 'universal primer' may have a sequence as follows:

```
GTGTAGCGTGAAGACGACAGAAAGGGCG.        (SEQ ID NO: 2)
```

An amplification reaction can be carried out as follows: for the first few cycles a low annealing temperature allows the degenerate primer to initiate priming and extension; for the followed cycles under a high annealing temperature the universal primer takes over and is used for amplification.

In certain embodiments, primers can include one or more moieties incorporated into 3' or 5' terminus or internally of primers that allow for detection or affinity separation.

Detection Probes

Detection probes are labeled oligonucleotides comprising sequence complementary to a target sequence, a primer sequence or primer extension product. The complementary portion of a detection probe can be any length that supports specific and stable hybridization between the detection probe and the target. For this purpose, a length of 10 to 40 nucleotides is preferred, with a complementary portion of a detection probe 16 to 25 nucleotides long being most preferred. Detection probes can comprise any of the detection labels. Some nucleotide or nucleotide analog which has fluorescence or quencher activity can be used as detection labels, for example guanosine base. Examples of detection labels may be fluorescent dye or non-fluorescent dye. The fluorescent dye may be a fluorophore which is quenched or emits fluorescence upon hybridization of primer or probe to a primer extension product. More than one probe may be needed for detecting the amplified product. Some primer may serve as primer and probe function. The probe(s) or primer hybridize to a target sequence or a primer sequence or the primer extension product, whereby generating detectable signal (FIG. 3). The hybridization may bring two detection labels into close proximity (FIGS. 3 A, B, E, F, G, H and I). The hybridization may bring two detection labels away from close proximity (FIG. 3 D).

In one aspect, a primer may have dual function serving as both primer and probe. For example, any one of the amplification primers may comprise detection labels that generate detection signal upon hybridization with target sequence. In one embodiment, a detection system is provided for detecting a target nucleic acid sequence in a sample. Such system comprises a linker-primer which comprises a 5' linker sequence, wherein said linker sequence is complementary to a part of target sequence or target derived sequence. The linker-primer comprises 5' additional sequence and/or 3' additional sequence flanking the linker sequence, wherein one or two of probes comprise sequences complementary to said additional sequences of the linker-primer, wherein one or two of probes comprise sequences complementary to a part (s) of target sequence or target derived sequence. Upon hybridization the double stranded stem structure formed by linker sequence and target sequence brings two or more detection labels of the probes into close or substantially close proximity (FIGS. 3A, B, E, F, J, K, L, M and N). It is appreciated that in the above detection system the linker-primer may simply function as probe. The linker portions of some of linker-primers that are in excess amount in a reaction and are not incorporated into a primer extension product may hybridize to a target sequence and bring detection labels into close proximity, therefore generating detection signals. In this case, the 3' target complementary portion of the linker primer is not needed and its 3' end may be blocked (FIGS. 3L and M).

In another aspect, the single-stranded end product is hybridised to a probe which comprises a nuclease sensitive portion (FIG. 3O). Upon becoming double stranded, the nuclease sensitive portion is cleaved so that a detection signal is generated. It is advantageous to use this type of probe as the probe can be repeatedly hybridised to the single-stranded end product and repeatedly cleaved. Such a probe, for example, can be a RNA probe or a chimera probe comprising RNA and DNA. When this probe forms a hybrid with the complementary sequence of the single-stranded end product, a ribonuclease specifically cuts the RNA region of this probe, resulting in emission of detection signal. An example of a ribonuclease useful in the practice of this invention is RNase H. RNase H is a RNA specific digestion enzyme which cleaves RNA found in DNA/RNA hybrids in a non-sequence-specific manner. Other ribonucleases and enzymes may be suitable to nick or excise RNA from RNA/DNA strands, such as Exo III and reverse transcriptase.

C. Enzyme

The disclosed methods make the use of polymerase for amplification. It is preferred that a DNA polymerase be capable of displacing the strand complementary to the template strand, termed strand displacement, and lack a 5' to 3' exonuclease activity. Strand displacement is necessary to result in synthesis of multiple copies of the target sequence per template molecule. It is preferred that DNA polymerases for use in the disclosed method are highly processive. It is particularly preferred that the DNA polymerase is a thermostable DNA polymerase. Preferred DNA polymerases are Taq DNA polymerase, Bca polymerase (Takara), Bst polymerase (NEB), Pfx50 polymerase (Invitrogen), Vent (exo-) DNA polymerase (NEB) and Tfu DNA polymerase (Qbiogene). It is preferred that Vent (exo-) DNA polymerase (NEB), Tfu DNA polymerase or Pfx50 polymerase are used. In the detection process, for extending one or more labeled nucleotides, both thermostable and non-thermostable DNA polymerase can be used.

Strand displacement can be facilitated through the use of a strand displacement factor, such as a helicase. It is considered that any DNA polymerase that can perform strand displacement in the presence of a strand displacement factor is suitable for use in the disclosed method, even if the DNA polymerase does not perform strand displacement in the absence of such a factor. Strand displacement factors useful in this invention include BMRF1 polymerase accessory subunit (Tsurumi et al., J. Virology 67(12):7648-7653 (1993)), adenovirus DNA-binding protein (Zijderveld and van der Vliet, J. Virology 68(2):1158-1164 (1994)), herpes simplex viral protein ICP8 (Boehmer and Lehman, J. Virology 67(2):711-715 (1993); Skaliter and Lehman, Proc. Natl. Acad. Sci. USA 91(22):10665-10669 (1994)), single-stranded DNA binding proteins (SSB; Rigler and Romano, J. Biol. Chem. 270:8910-8919 (1995)), and calf thymus helicase (Siegel et al., J. Biol. Chem. 267:13629-13635 (1992)).

Any nuclease that can act on a double-stranded nucleic acid generated by extension from a cleavable linker-primer as described above, that has been annealed to a nucleic acid as a template and degrades the linker-primer sequence completely or partially from the extended strand to effect a strand displacement reaction, may be used in the present invention. That is, the nuclease is an enzyme that can degrade the linker-primer part of the double-stranded DNA. Examples of nucleases that can be used in the present invention include, but are not limited to, ribonucleases. Among these, ribonuclease H (RNase H) which acts on an RNA portion of a double-stranded nucleic acid composed of a DNA and an RNA can be preferably used. Any ribonuclease that has the above-mentioned activities can be preferably used in the present invention, including mesophilic and heat-resistant ones. For example, an RNase H from *E. coli* can be used for a reaction at about 50° C. to about 70° C. in the method of the present invention. A heat-resistant ribonuclease can be preferably used in the method of, the present invention. Examples of the heat-resistant ribonucleases which can be preferably used include, but are not limited to, a commercially available ribonuclease, Hybridase™ Thermostable RNase H (Epicenter Technologies) as well as an RNase H from a thermophilic bacterium of the genus *Bacillus*, a bacterium of the genus *Thermus*, a bacterium of the genus *Pyrococcus*, a bacterium of the genus *Thermotoga*, a bacterium of the genus *Archaeoglobus* or the like. Furthermore, both of naturally occurring ribonucleases and variants can be preferably used.

The RNase H is not limited to a specific one as long as it can be used in the method of the present invention. For example, the RNase H may be derived from various viruses, phages, prokaryotes or eukaryotes. It may be either a cellular RNase H or a viral RNase H. The cellular RNase H is exemplified by *Escherichia coli* RNase HI and the viral RNase H is exemplified by HIV-1 RNase H. Type I, type II or type III RNase H can be used in the method of the present invention. For example, RNase HI from *Escherichia coli*, or RNase HII from a bacterium of the genus *Pyrococcus* or a bacterium of the genus *Archaeoglobus* is preferable, without limitation.

II Method

The disclosed methods involve at least two forward primers annealing to one strand of target sequence and at least one reverse primer annealing to the complementary strand of target sequence, extension and strand displacement by DNA polymerase, further extension on the displaced strand, separating the primer extension products from the templates on which they are synthesized to produce single-stranded or partially single-stranded molecules; and treating the single-stranded molecules generated with the forward and reverse primers under hybridizing and extension conditions such that a primer extension product is synthesized using each or some of the single stranded molecules as a template. The disclosed methods may also involve one or more linker-primers that comprise a linker blocking moiety and/or a linker sequence and/or a cleavable linker. The steps of the reaction may be carried out stepwise or simultaneously and can be repeated as often as desired.

One method of the invention is provided for amplifying and detecting a target nucleic acid sequence of interest in a sample, wherein said target nucleic acid comprises one strand or two separate complementary strands, the method comprising the steps of:

(a) treating the sample with at least two oligonucleotide primers capable of hybridizing to a first strand of the target sequence and at least one oligonucleotide primer capable of hybridizing to a second strand of the target sequence complementary to the first strand, under hybridizing condition such that for each strand of the target nucleic acid sequence to which each oligonucleotide primer is hybridized and under extension condition such that an extension product of each primer is synthesized which is complementary to each nucleic acid strand, wherein said at least two oligonucleotide primers comprises one outer primer and one or more inner primers, which hybridize to target sequence in 5' to 3' order, wherein one or more of said primers comprises a linker blocking moiety and/or a 5' linker sequence and/or a cleavable linker;

(b) separating the primer extension products from templates to produce single-stranded molecules;

(c) treating the single-stranded molecules generated from step (b) with the primers of step (a) under hybridizing and extension conditions such that a primer extension product is synthesized using the single stranded molecules produced in step (b) as a template; and (d) repeating steps (b) and (c) at least once.

Separating two complementary strands of the target nucleic acid may be accomplished by physical, chemical or enzymatic means. It is preferred that the separating is accomplished by strand displacement and/or heating.

For exponential amplification at least two forward primers and at least one reverse primer are used for amplification, while for linear amplification, at least two forward primers are used for amplification. The at least two forward primers, including one outer primer and one or more inner primer, hybridize to different places on one strand of the target sequence. The outer primers are not linker-primers, allowing exponential amplification to occur. The region of the target sequence with substantial complementarity to the outer primer is known as the outer primer target region or outer forward primer target region, and similarly for other primers, and region of the target sequence to which they anneal. The outer primer target region is 3' of the inner primer target region. The distance between the outer primer target region and inner primer target region can be any length. There may be even an overlap of the outer primer target region and inner primer target region. Upon target specific hybridization, under extension condition each primer is extended by a DNA polymerase. The inner primer extension product is displaced by a strand displacement activity of an enzyme. It is preferred that the strand displacement activity is provided by the same DNA polymerase used for primer extension. Alternatively, the strand displacement activity may be provided by another enzyme.

In the steps (a) and (c) the hybridizing condition and extension condition may be the same condition. The hybridizing condition and extension condition may share the same environment including the same temperature. Alternatively, the hybridizing condition and extension condition are the different conditions and are repeated at least once, wherein the temperature, buffer or other feature of the environment can be adjusted to suit the further extension and strand displacement. For example, the extension temperature can be 72° C., while the hybridizing temperature can be 50-60° C. The alteration or oscillation between the hybridization and extension condition can be performed as many times as required. The primer extension and strand displacement both occur under extension condition. The strand displacement may be accomplished by an agent which promotes a strand displacement activity. It is preferred that the primer extension activity and strand displacement activity are provided by a DNA polymerase. It is more preferred that the DNA polymerase is a thermostable DNA polymerase. Example of the preferred thermostable DNA polymerase is Vent(exo-), Pfx50 or Tfu DNA polymerase. Depending on how many inner primers are available for each target strand, the extension and strand displacement continue until all or substantially all single stranded primer extension molecules become double stranded.

The double stranded molecules formed by the primer extension reaction are separated to become single stranded molecules. This separation can be accomplished by any means which is known in the art, which can be physical, chemical, or enzymatic means. In one embodiment, such separation is accomplished by the strand displacement which occurs during primer extension under extension condition. In this case, step (b) is merged with step (c) and step (a), in other words, all steps are occurring homogenously and cannot be distinguished from each other. Such reaction, for example, can be isothermal amplification. In another embodiment the separation is accomplished by denaturing, which can be caused by heating. It is known in the art that suitable temperature can be used for heating denaturing. An example of the heating temperature is 94° C. In a further embodiment, the separation of the primer extension products from templates is accomplished by the combination of strand displacement and denaturing. Under extension condition, the inner primer extension strand is displaced by the extension of outer primer and becomes single-stranded. The single-stranded inner primer extension product may be hybridised by another primer which is extended using the inner primer extension product as template. The double-stranded products may not be able to subject to a further strand displacement, therefore, the only way to separate them is denaturing, which is preferably heating at high temperature.

One or more primers may comprise a linker which plays a role so that a single-stranded end product is generated. In one embodiment (FIG. 2A), the linker is a blocking moiety which is incorporated into the primer or into the priming portion of the primer. It is preferred that one of inner primers is the linker-primer. The whole or part of the inner linker-primer cannot be copied (replicated) during amplification due to the blocking moiety, in other words, a primer extension using the linker-primer extension product as template will stop at the blocking moiety, whereby the reaction will accumulate the single-stranded primer extension product generated on templates of the linker-primer extension product.

Figure 2G:
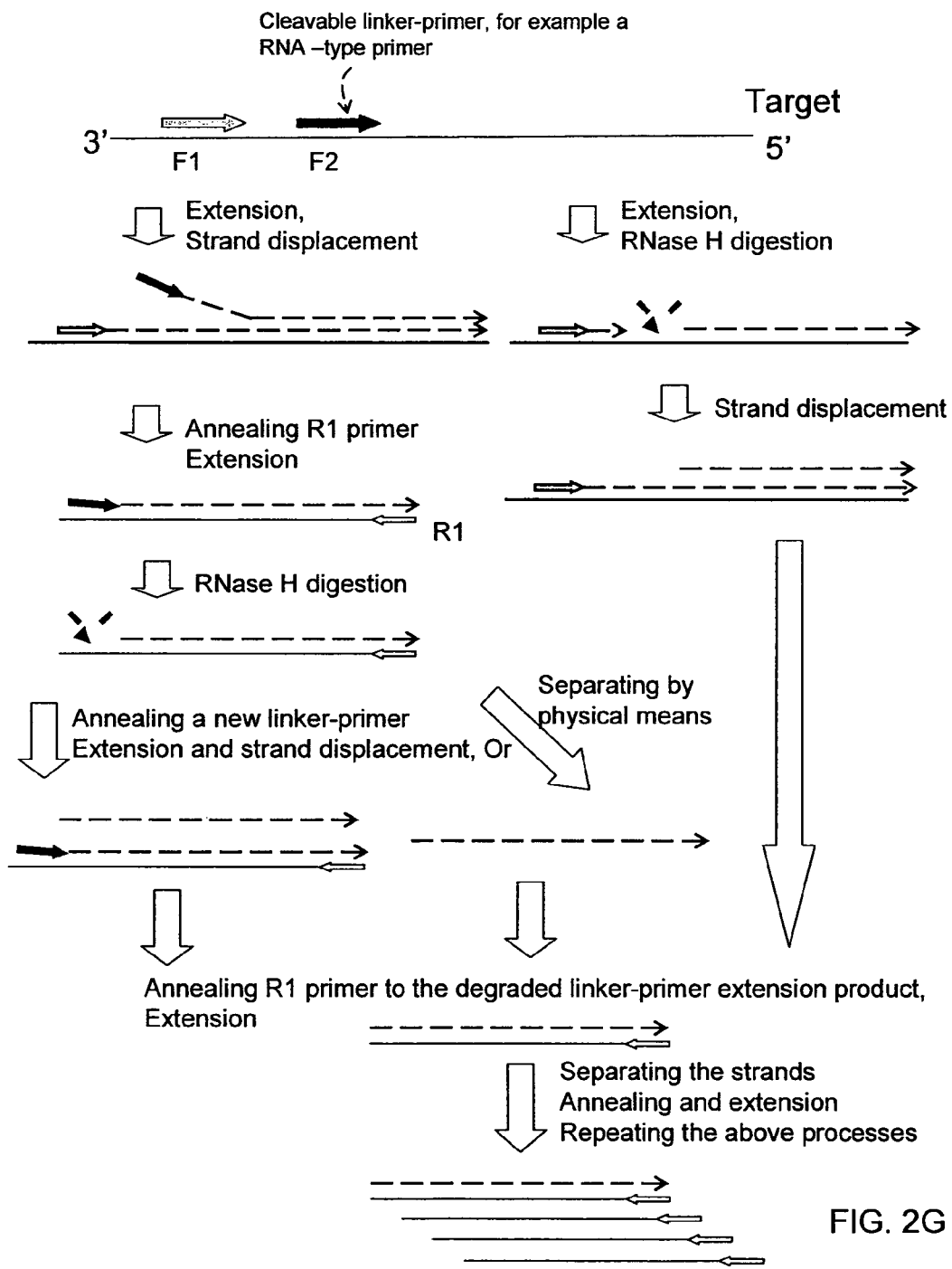
Figure 3:
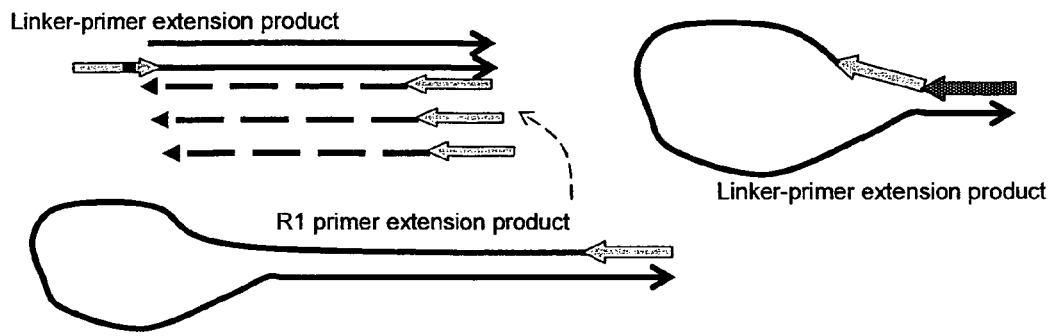
FIG. 3 illustrates various probes and their interactions with single-stranded end products. (A) Two separate probes attached with detection labels hybridize to the single-stranded end product. The detection labels are brought into close proximity by the double stranded stem structure. (B) One single probe is attached with a detection label; while the linker-primer is attached with another detection label. Upon hybridization between the probe and the folded linker-primer extension product, the two labels are brought into close proximity. (C) One single probe is attached with a detection label and hybridizes to the single stranded end product. (D) A molecular beacon probe hybridizes to the loop portion of the single-stranded end product. (E) The linker-primer comprises an additional portion at its 5' end which may be not complementary or identical to the target sequence. The 5' additional portion sequence may not comprise similar or substantially complementary to the whole or part sequence of any primer. Upon forming a stem-loop structure, the additional portion remains single stranded so that a probe can hybridize to the additional portion. Both strands on the right side of the double-stranded stem portion may be single stranded. This figure shows that both strands on the right side of the double-stranded stem portion are hybridized with probes and bring two labels into close proximity. (F) The linker-primer comprises an additional sequence 3' of the linker sequence. A labelled probe hybridizes to the additional sequence 3' of the linker sequence. Two detection labels are brought into close proximity by the double stranded stem structure. (G) Two separate probes tagged with detection labels hybridize to the single-stranded end product. The detection labels are brought into close proximity by the single stranded loop portion. (H) One probe tagged with two detection labels at both ends hybridizes to the single-stranded end product. The detection labels are brought into close proximity by the single stranded loop portion. (I) A detection probe hybridizes to the linker-primer extension strand in the close proximity or to adjacent regions with the linker sequence of the linker primer, whereby generating a detection signal. (J) and (K) A detection system for detecting a target nucleic acid sequence in a sample comprising primers and detection probes is illustrated. The linker-primer comprises 5' additional sequence and/or 3' additional sequence flanking the linker sequence. One probe (J) or two probes (K) comprise sequences complementary to the additional sequences of the linker-primer. One (J) or two (K) probes comprise sequences complementary to a part (s) of target sequence or target derived sequence. Upon hybridization the double stranded stem structure formed by linker sequence and the target sequence brings two or more detection labels of the probes into close or substantially close proximity. (L) and (M) illustrate that the linker-primer may simply function as probe. The linker portions of some of linker-primers that are in excess amount in a reaction and are not incorporated into a primer extension product may hybridize to a target sequence and bring detection labels into close proximity, therefore generating detection signals. In this case, the 3' target complementary portion of the linker-primer is not needed and its 3' end may be blocked. (N) The linker sequence of a linker-primer extension product is digested by a nuclease that possesses a nuclease activity for a double stranded nucleic acid. This digestion generates a detection signal. (O) The single-stranded end product is hybridised to a probe which comprises a nuclease sensitive portion. Upon becoming double-stranded, the nuclease sensitive portion is cleaved so that a detection signal is generated.
Figure 3:
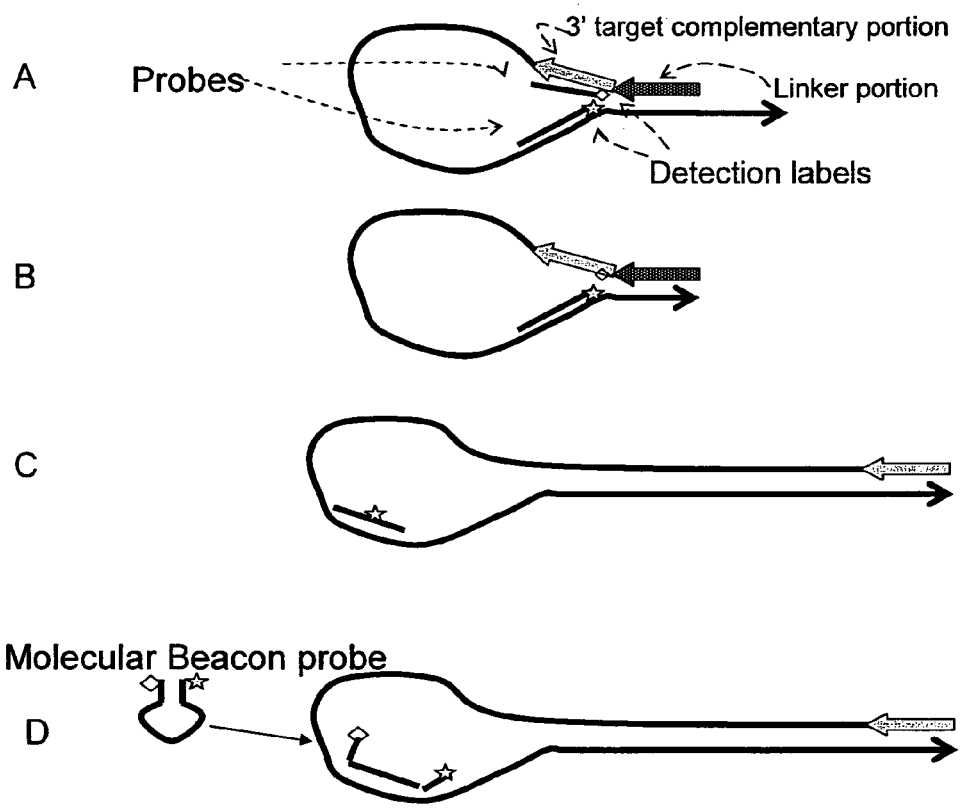
Figure 3:
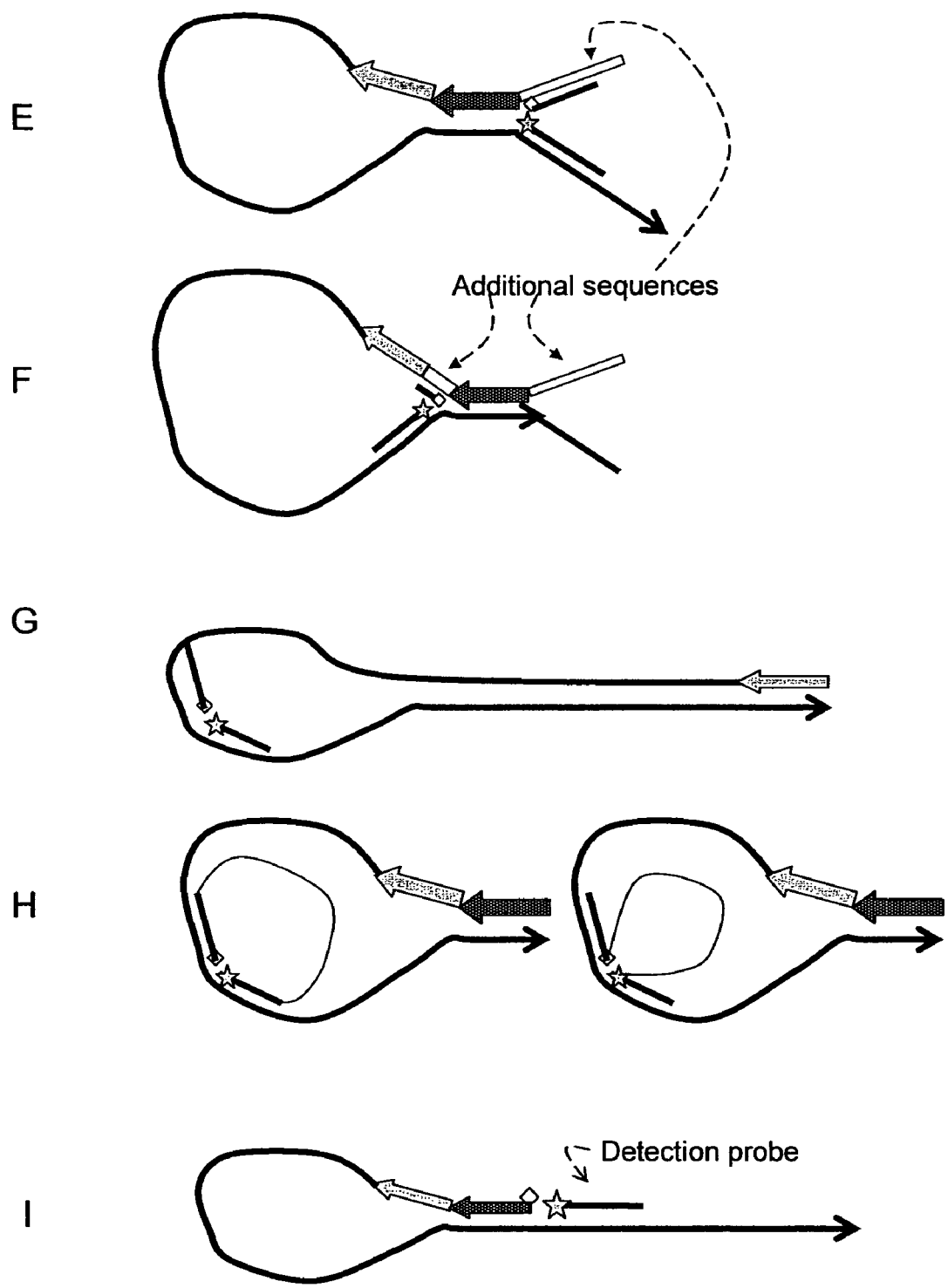
Figure 3:
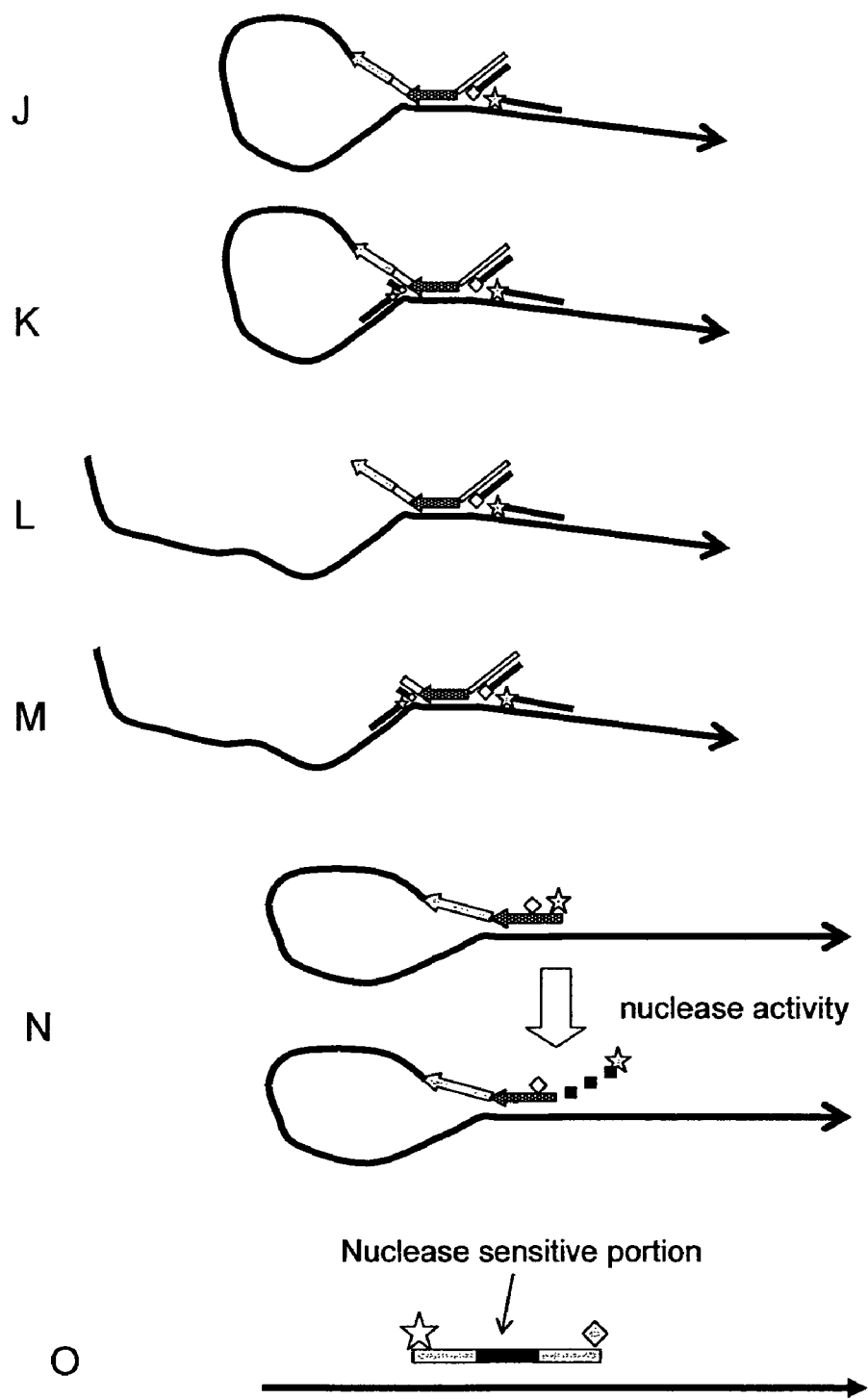
Figure 4:
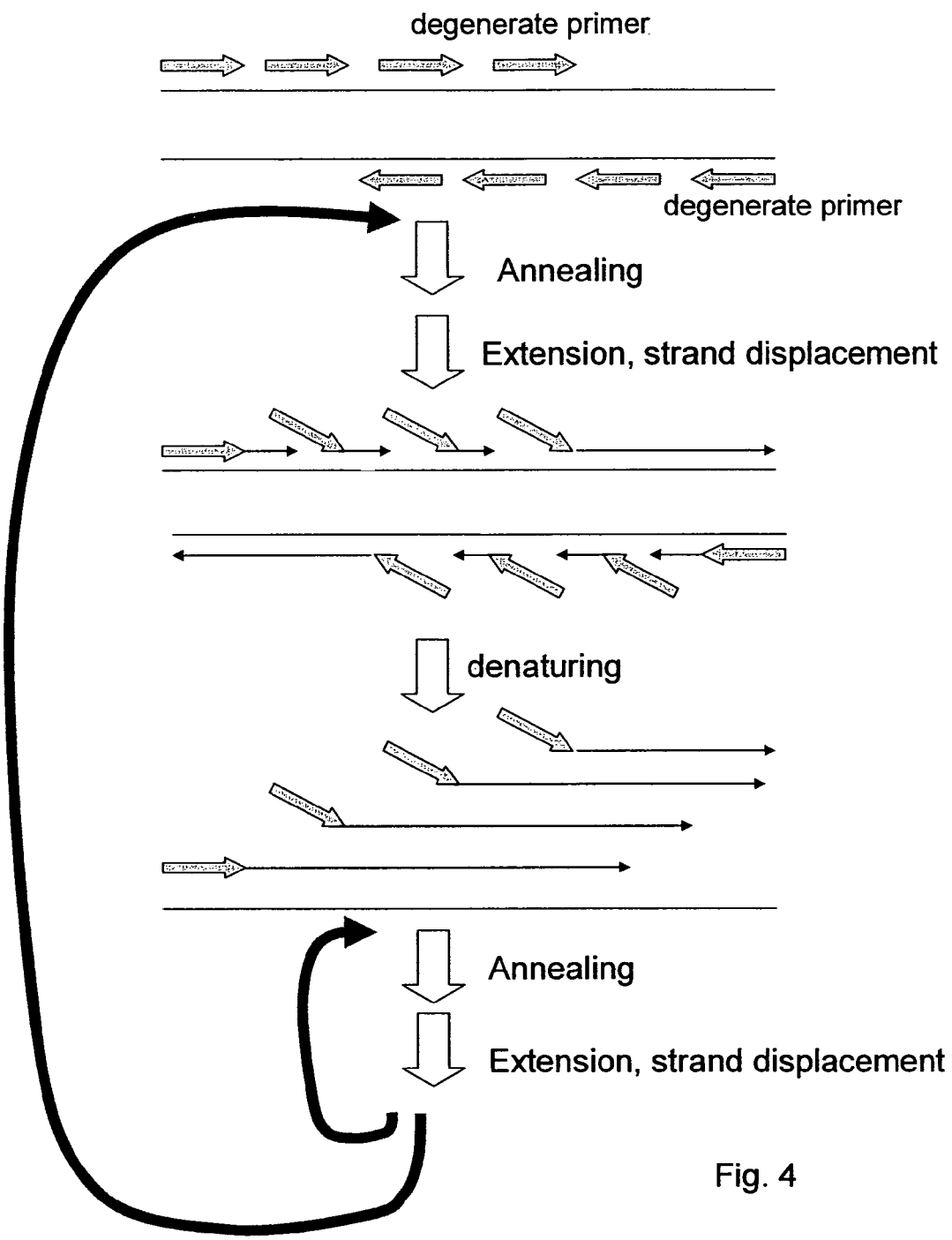
FIG. 4 illustrates a method for amplifying any stretch of nucleic acid sequence using degenerate primers (a plurality of random oligonucleotide primers). A target nucleic acid sample comprising two separate complementary strands is mixed with degenerate primer. Under hybridizing condition the primers anneal to many places of the target sequence. Under extension condition an extension product of each primer is synthesized which is complementary to each nucleic acid strand. The down stream primer extension products are displaced by upstream primer extension reaction. The strand displaced primer extension products are again subjected to hybridizing condition and extension condition, which are repeated at least once. The double stranded molecules formed by the primer extension reaction are denatured. The denatured single stranded molecules are treated with the same primers above under hybridizing and extension conditions such that primer extension products are synthesized. The hybridizing and extension conditions are repeated at least once. Then the steps, denaturing and the repeated hybridizing and extension conditions, are repeated at least once.

In another embodiment, the linker-primer comprises a cleavable linker (FIG. 2G). Thus, the linker-primer is a cleavable primer, which is cleaved on the linker site or degraded completely or partially by an enzymatic agent when the linker primer forms a hybrid with its complementary nucleic acid sequence, wherein the enzymatic agent comprises an RNase H activity when said linker-primer is RNA-type primer made of ribonucleotides and/or modified ribonucleotide. The cleavable linker-primer may be a chimeric primer comprising ribonucleotides and non-ribonucleotides. In an example depicted in FIG. 2G, one inner forward primer (F2) is a cleavable linker-primer which is a RNA-type primer. In one pathway, during primer extension and strand displacement, the F2 primer extension strand is displaced. The displaced F2 primer extension strand is hybridised by a reverse primer R1 which is extended by a DNA polymerase using the F2 primer extension strand as template. The RNA part of F2 primer on the double-stranded hybrid RNA/DNA formed by the R1 primer extension is recognised and cleaved by RNase H. The degradation by RNase H releases the F2 primer binding site, whereby a new F2 is hybridised to the previous F2 binding site and initiates a new extension. The process of degradation, annealing and extension repeats many times to produce many copies of the F2 primer extension product which lacks a part of or the whole F2 primer sequence. In another pathway, after annealing and extension of the F2 primer on the template, the F2 primer sequence is degraded immediately before being displaced by the extension of the F1 primer. Thus in the subsequent strand displacement, the F2 primer extension product which lacks the part or whole of the F2 sequence is displaced and available for the next round of primer extension. One or more reverse primers annealed to the F2 primer extension product which lack the F2 sequence are extended and displaced (or separated from the template). The above processes are repeated many times, whereby single-stranded end products are generated.

It should be appreciated that a reaction may include a first linker-primer with a blocking moiety for the first strand of a target nucleic acid and a second linker-primer with cleavable moieties for the second strand of the target nucleic acid which is complementary to the first strand of the target nucleic acid. Following the above example, if the R1 primer is the second linker-primer with a blocking moiety, the reaction may accumulate the F2 primer extension product as a single-stranded end product which lacks the F2 primer sequence and lacks the binding site for the R1 primer.

In another embodiment (FIGS. 2B, C, D and E), the linker is a 5' linker sequence which is complementary to a part of target sequence or target derived sequence. The linker sequence may hybridize to a part of sequence in the linker-primer extension product. The linker sequence may comprise identical or substantially identical to the sequence of one of other primers. It is preferred that the linker sequence is identical or substantially identical to the sequence of one of the primers for the complementary strand of the target sequence.

Some primer extension products, upon becoming single-stranded and under hybridizing conditions, fold (self annealing) to form a stem-loop structure, which is preferably detected in a detection system. The double stranded stem portion comprises all or part of a primer binding site and thereby prevents or inhibits the annealing of a corresponding primer. In one embodiment (FIGS. 2C and E), the linker-primer extension product, upon becoming single stranded, folds to form a stem-loop structure, wherein the linker sequence of the linker-primer comprises a sequence identical or substantially identical to the inner primer, the target sequence of which is the most 3' of the primer target sequence or binding site on that strand ("inner most primers"), wherein the formed double stranded stem portion comprises primer binding site which prevent a corresponding primer annealing, wherein the loop portion lacks other primer binding site, thereby accumulating the single stranded end product. In another embodiment (FIGS. 2B and E), the R1 primer extension molecule generated on the template of the linker-primer extension molecule folds to form a stem-loop structure ("the first R1 primer extension molecule"), wherein the 3' end of the first R1 primer extension molecule anneals to itself and primes an extension. At the same time, the linker-primer anneals to the first R1 primer extension molecule and primes an extension which subsequently displaces the strand generated from the 3' end of the first R1 primer extension molecule, thereby opening up the stem-loop structure. Upon opening up the stem-loop structure of the first R1 primer extension molecule, the R1 primer anneals to 3' end of the first R1 primer extension molecule and initiates to synthesize a second R1 primer extension molecule, which displaces the linker-primer extension strand. The displaced linker-primer extension strand acts as a template for a further primer extension. The second R1 primer extension molecule, upon subjecting to denaturing and hybridizing conditions, folds to form a stem-loop structure which does not contain an available primer binding site, whereby the reaction is accumulating this structure and the loop part is suitable for a probe binding in a detection system.

If the distance between the linker sequence and its complementary sequence on the linker-primer extension product is in a suitable range, the forming stem-loop structure is kinetically favored. Normally, the shorter the distance the more favored the stem-loop structure. Generally, less than 300 nt is favored, and more favored less than 200 nt, and even more favored less than 100 nt.

The linker-primer may comprise additional sequence at 5' or 3' of the linker sequence that is not identical or complementary to either strand of the target sequence. The additional sequence may support a detection process and/or an amplification process. It is preferred that the additional sequence is complementary to a detection probe. The specific hybridization between linker sequence and target sequence, between detection probe and target sequence, and between detection probe and the additional sequences of the primer is detected via detectable change in a detection system. Such hybridization may bring two or more detection labels into close or substantially close proximity. Such proximity may emit detection signals (FIGS. 3J, K, L, and M).). It is appreciated that in the above detection system the linker-primer may simply function as probe. The linker portions of some of linker-primers that are in excess amount in a reaction and are not incorporated into a primer extension product may hybridize to a target sequence and bring detection labels into close proximity, therefore generating detection signals. In this case, the 3' target complementary portion of the linker primer is not needed and its 3' end may be blocked (FIGS. 3L and M).

If a method of the present invention is not carried out under isothermal condition, the steps (b) and (c) are repeated at least once. It is preferred that the steps (b) and (c) are repeated more than 10 times. It is even preferred that steps are repeated more than 20 times.

In one embodiment, a method is provided for amplifying and detecting a target sequence of a nucleic acid of interest in a sample,
wherein the nucleic acid of interest comprises one strand or two separate complementary strands
the method comprising the steps of:
(a) amplifying the target sequence by an amplification method in the presence of an oligonucleotide linker-primer, which linker-primer comprises a linker, which may be a blocking moiety and/or a cleavable moiety and/or a 5' linker sequence, whereby a single stranded end product is generated;
(b) detecting the primer extension product resulting from the amplification by hybridizing the single stranded end product to a probe.

In another embodiment, a method is provided for amplifying and optionally detecting a target sequence of a nucleic acid of interest in a sample,
wherein the nucleic acid of interest comprises one strand or two separate complementary strands
the method comprising the steps of:
(a) amplifying the target sequence by an amplification method in the presence of an oligonucleotide linker-primer, which linker-primer comprises:
 (i) a priming portion capable of hybridizing to the first strand template of the target sequence,
 (ii) a linker sequence 5' to the priming portion which is complementary or substantially complementary to the linker-primer extension product, and optionally to a part of a second strand of the target sequence, which second strand is complementary to the first strand,
(b) detecting the primer extension product resulting from the amplification by hybridizing the linker sequence of the linker-primer to the primer extension product,
wherein a double stranded stem structure formed by the hybridizing brings two or more detection labels into close or substantially close proximity or increases the distance of two detection labels.

In the above methods of the invention, the amplification method can be any suitable amplification method. One type of the amplification methods can be an isothermal amplification method, which includes, but is not limited to, LAMP, SDA, ICAN, RCA or NASBA. In an example depicted in FIG. 2F, in a LAMP or LAMP-like reaction a linker-primer with a blocking moiety or cleavable moiety hybridises to any region of the target nucleic acid to be amplified between F3C and R3. It is particularly preferred that the linker-primer is a loop primer or boost primer hybridising to a first strand or second strand of the target region between F2C and F1C or R1 and R2. Another amplification method is an amplification method with cycling temperatures, for example PCR or the amplification method provided in this invention.

It should be appreciated that the methods of the present invention can be, or are preferably used for amplifying and detecting multiple target nucleic acid sequences in a single reaction. In this case, a set of primers or probe for each target sequence is included in the reaction mixture. The primer or probe for each target sequence may be labeled differently or attached to a solid support to aid in detection of different targets.

The method of the invention may further comprise detecting the reaction products. It is preferred that the detecting is real time detecting. The double stranded amplification product can be conveniently detected by a double strand specific dye such as SYBR green. The linker-primer may comprise detection label. The detection may comprise detecting the single-stranded end product. The detection may be through use of detection label, for example through the use of probes tagged with a detection label. The detection label may be a fluorescent or non-fluorescent dye which is attached to any nucleotide or nucleotide analog in the primer or probe. The fluorescent dye may be a fluorophore which is quenched or emits fluorescence upon hybridization of primer or probe to the extension product. The probes may hybridize to the linker-primer extension product, thereby generating detectable signal. The hybridization may bring two detection labels into close or substantially close proximity, for example to modify their combined fluorescence characteristics by Fluorescence Resonance Energy Transfer (FRET). One probe may be labeled with an acceptor fluorophore and the other probe may be labeled with a donor fluorophore of a fluorescence energy transfer pair. Upon hybridization of the two probes with their complementary sequences, the donor and acceptor fluorophores are within a certain distance so that a detection signal is generated by exciting the sample with light at a wavelength absorbed by the donor fluorophore and fluorescent emission from the fluorescence energy transfer pair. Alternatively, the hybridization may increase the physical distance between two detection labels.

In another embodiment of the invention, the linker-primer with linker sequence or a combination of the linker-primer and probes can be used for detecting a target nucleic acid sequence amplified by any method. For example, a PCR may be carried out in the presence of a linker-primer, wherein the 5' linker sequence of the linker-primer is complementary or substantially complementary to a part of sequence on the linker-primer extension product. Detecting the linker-primer extension product can be achieved through separating the linker-primer extension product from the template, hybridizing the linker sequence to the linker-primer extension product, wherein a double stranded stem structure formed by said hybridizing brings two or more detection labels into close or substantially close proximity or increase the distance of two detection labels. In this method, it is preferred that the linker-primer comprises a 5' additional sequence and/or 3' additional sequence flanking the linker sequence. The additional sequence is used to hybridize to a labeled detection probe. As the additional sequence can be an universal sequence, many different primers or probes may comprise this universal additional sequence, the detection probe complementary to this additional sequence can be shared and be reused, therefore achieving a significant cost-saving. It is also desirable that both 5' additional and 3' additional sequence may comprise identical sequence if both are present. Other target specific probes may be used to hybridize to a particular place in target derived sequence, preferable a primer extension product. The linker sequence is designed so that, when the linker sequence hybridizes to the primer extension product, the double stranded linker portion formed by the linker sequence and its target sequence bring the detection labels into close proximity. Several examples of this design are shown in FIG. 3.

To aid in detection and quantification of nucleic acids amplified using the disclosed methods, detection labels can be incorporated into primer, or amplified nucleic acids. As used herein, a detection label is any molecule that can be associated or added to primer or amplified nucleic acid, directly or indirectly, and which results in a measurable, detectable signal, either directly or indirectly. Many such labels for incorporation into nucleic acids or coupling to nucleic acid probes are known to those of skill in the art.

Examples of detection labels suitable for use in the disclosed method are radioactive isotopes, fluorescent dye, non-fluorescent dye, phosphorescent molecules, enzymes, antibodies, and ligands.

As well as an exponential or non-linear amplification method, the invention also provides a linear amplification method. The method comprises the steps of:
(a) treating the sample with at least two forward oligonucleotide primers that hybridize to different places of one strand of the target sequence, wherein there is no reverse oligonucleotide primer for the complementary strand of the target sequence, under hybridizing conditions such that for each strand of the target nucleic acid sequence to which each oligonucleotide primer is hybridized and under extension condition an extension product of each primer is synthesized which is complementary to each nucleic acid strand, wherein none or one or more of said primers comprises a linker sequence, wherein said hybridizing condition and extension condition are repeated at least once;
(b) separating (denaturing) the primer extension products to produce single-stranded molecules;
(c) treating the single-stranded molecules generated from step (b) with the primers of step (a) under hybridizing and extension conditions such that a primer extension product is synthesized using the single stranded molecules produced in step (b) as a template, wherein said hybridizing condition and extension condition are repeated at least once; and
(d) repeating steps (b) and (c) at least once.

In another embodiment of the invention, a method is provided for amplifying and detecting a target nucleic acid sequence of interest in a sample, wherein said target nucleic acid comprises one strand or two separate complementary strands, the method comprising the steps of:
(a) treating the sample with two primers capable of hybridizing to a first strand of the target sequence and one primer capable of hybridizing to a second strand of the target sequence complementary to the first strand, under hybridizing condition such that for each strand of the target nucleic acid sequence to which each primer is hybridized and under extension condition such that an extension product of each primer is synthesized which is complementary to each nucleic acid strand, wherein said hybridizing condition and extension condition are repeated at least once, wherein said extension condition permits primer extension and strand displacement activity;
(b) separating (denaturing) the primer extension products to produce single-stranded molecules;
(c) treating the single-stranded molecules generated from step (b) with the primers of step (a) under hybridizing and extension conditions such that a primer extension product is synthesized using the single stranded molecules produced in step (b) as a template, wherein said hybridizing condition and extension condition are repeated at least once, wherein said extension condition permits primer extension and strand displacement activity; and
(d) repeating steps (b) and (c) at least once, In this embodiment, the amplification achieves more than two fold increase of the amount of said target nucleic acid sequence at each cycle through repeating steps (b) and (c). A theoretical calculation of the amplification rate for this method is as follows: assuming the initial quantity of template is, $N_0$, the population size at cycle n is, $N_n = N_0(2^n + n2^{n-1})$.

In a further embodiment of the invention, a method is provided for amplifying and detecting a target nucleic acid sequence of interest in a sample, wherein said target nucleic acid comprises one strand or two separate complementary strands, the method comprising the steps of:
(a) treating the sample with three primers capable of hybridizing to a first strand of the target sequence and one primer capable of hybridizing to a second strand of the target sequence complementary to the first strand, or with two primers capable of hybridizing to a first strand of the target sequence and two primers capable of hybridizing to a second strand of the target sequence complementary to the first strand under hybridizing condition such that for each strand of the target nucleic acid sequence to which each primer is hybridized and under extension condition such that an extension product of each primer is synthesized which is complementary to each nucleic acid strand, wherein said hybridizing condition and extension condition are repeated at least once, wherein said extension condition permits primer extension and strand displacement activity;
(b) separating (denaturing) the primer extension products to produce single-stranded molecules;
(c) treating the single-stranded molecules generated from step (b) with the primers of step (a) under hybridizing and extension conditions such that a primer extension product is synthesized using the single stranded molecules produced in step (b) as a template, wherein said hybridizing condition and extension condition are repeated at least once, wherein said extension condition permits primer extension and strand displacement activity; and
(d) repeating steps (b) and (c) at least once, In this embodiment the amplification achieves more than two fold increase of the amount of said target nucleic acid sequence at each cycle through repeating steps (b) and (c).

In a further embodiment of the invention, a method is provided for amplifying and detecting a target nucleic acid sequence of interest in a sample, wherein said target nucleic acid comprises one strand or two separate complementary strands, the method comprising the steps of:
(a) treating the sample with at least three primers capable of hybridizing to a first strand of the target sequence and at least two primers capable of hybridizing to a second strand of the target sequence complementary to the first strand, under hybridizing condition such that for each strand of the target nucleic acid sequence to which each primer is hybridized and under extension condition such that an extension product of each primer is synthesized which is complementary to each nucleic acid strand, wherein said hybridizing condition and extension condition are repeated at least once, wherein said extension condition permits primer extension and strand displacement activity;
(b) separating (denaturing) the primer extension products to produce single-stranded molecules;
(c) treating the single-stranded molecules generated from step (b) with the primers of step (a) under hybridizing and extension conditions such that a primer extension product is synthesized using the single stranded molecules produced in step (b) as a template, wherein said hybridizing condition and extension condition are repeated at least once, wherein said extension condition permits primer extension and strand displacement activity; and
(d) repeating steps (b) and (c) at least once, In this embodiment, the amplification achieves more than two fold increase of the amount of said target nucleic acid sequence at each cycle through repeating steps (b) and (c).

In another embodiment of the invention, a method is provided for amplifying nucleic acid sequence of interest in a sample, the method comprising the steps of:
(a) treating the sample with a degenerate primer (a plurality of random oligonucleotide primers), under hybridizing condition such that the primer hybridizes to many places of nucleic acid to allow the formation of a nucleic acid-primer hybrid and under extension condition such that primer extension products are synthesized, wherein said degenerate primer comprises random or partially random nucleotides, wherein said hybridizing condition and extension condition are repeated at least once, wherein said extension condition permits primer extension and strand displacement activity;
(b) separating (denaturing) the primer extension products to produce single-stranded molecules;
(c) treating the single-stranded molecules generated from step (b) with the primers of step (a) under hybridizing and extension conditions such that primer extension products are synthesized using the single stranded molecules produced in step (b) as a template, wherein said hybridizing condition and extension condition are repeated at least once, wherein said extension condition permits primer extension and strand displacement activity; and
(d) repeating steps (b) and (c) at least once.

In another aspect, the degenerate primer comprises a non-random portion 5' of the random or partially random nucleotides. The amplification reaction comprises a degenerate primer and a universal primer. The universal primer comprises the non-random portion sequence of the degenerate primer.

Kits

The invention also extends to kits for performing a method of amplifying a target sequence described herein where the kit comprises at least said primers, preferably said linker-primer, and one or more further primers and probes. Kits will generally contain two or more reagents necessary to perform the subject methods. The reagents may be supplied in pre-measured amount for individual assays so as to increase convenience and/or reproducibility.

In one embodiment, the subject kits comprise primers and DNA polymerase. The kits of the invention may also include one or more additional reagents required for various embodiments of the subject methods. Such additional reagents include, but are not limited to: probes, buffers, nucleotides, and the like. Preferred kits are as defined in the claims appended hereto.

Any sub-titles herein are included for convenience only, and are not to be construed as limiting the disclosure in any way.

The invention will now be further described with reference to the following non-limiting Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

EXAMPLES

Example 1

All primers used in the subsequent experiments were synthesized by EUROGENTEC, UK. Primers were designed to amplify a target DNA sequence K10 3'UTR from a transgenic medfly line. This K10 sequence is derived from the fs(1)K10 gene of Drosophila melanogaster. The sequence of this gene fragment, as present in the transgenic medfly, comprises the sequence:

(SEQ ID NO: 3)

```
  1  ggagcttgat aacattatac ctaaacccat ggtcaagagt aaacatttct gcctttgaag 61  ttgagaacac aattaagcat cccctggtta aacctgacat tcatacttgt taatagcgcc 121  ataaacatag caccaatttc gaagaaatca gttaaaagca attagcaatt agcaattagc 181  aataactctg ctgacttcaa aacgagaaga gttgcaagta tttgtaaggc acagtttata 241  gaccaccgac ggctcattag ggctcgtcat gtaactaagc gcggtgaaac ccaattgaac
```

-continued

```
301  atatagtgga attattatta tcaatgggga agatttaacc ctcaggtagc aaagtaattt 361  aattgcaaat agagagtcct aagactaaat aatatattta aaaatctggc cctttgacct 421  tgcttgtcag gtgcatttgg gttcaatcgt aagttgcttc tatataaaca ctttccccat 481  ccccgcaata atgaagaata ccgcagaata aagagagatt tgcaacaaaa aataaaggca 541  ttgcgaaaac tttttatggg ggatcattac actcgggcct acggttacaa ttcccagcca 601  cttaagcgac aagtttggcc aacaatccta ctaatagcta atagcgcaat cactggtaat 661  cgcaagagta tataggcaat agaacccatg gatttgacca aaggtaaccg agacaatgga 721  gaagcaagag gatttcaaac tgaacaccca cagtactgtg tactaccact ggcgcgtttg 781  gg
```

Figure 5:
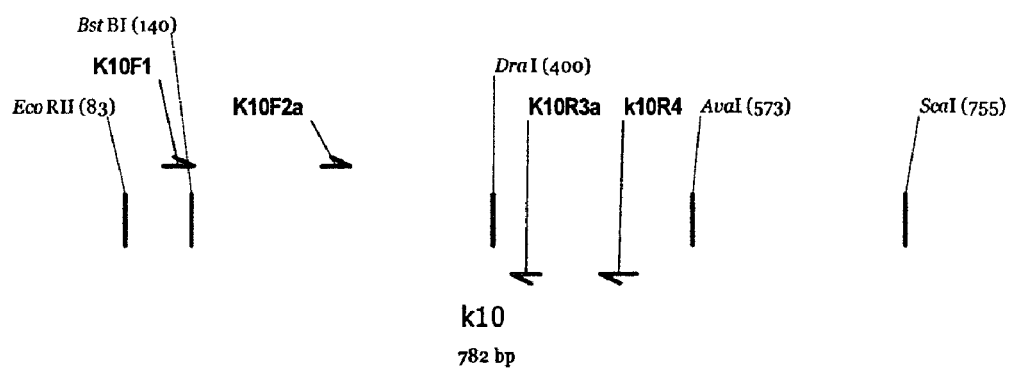
FIGS. 5 and 6 are examples of experiment designs and amplification products detected in agarose gels.
Figure 5:

The primer locations and orientations are shown in FIG. 5A. The sequences of primers are:

```
K10F1
GCGCCATAAACATAGCACCAATTTCG          (SEQ ID NO: 4)

K10F2A
GGCTCATTAGGGCTCGTCATGTAAC           (SEQ ID NO: 5)

K10R3A
CCAAATGCACCTGACAAGCAAGGTC           (SEQ ID NO: 6)

K10R4
GCAAATCTCTCTTTATTCTGCGGTATTCTTC     (SEQ ID NO: 7)
```

All nucleic acid sequences are written 5' to 3' unless otherwise stated.

Medfly genomic DNA samples were prepared by a standard extraction method (Molecular Cloning: A Laboratory Manual (3-Volume Set): Joseph Sambrook, David W. Russell). Primers were diluted to a final concentration of 10 µM.

Perform amplification using the following ingredients and conditions: 10×PCR Buffer (ThermoPol Reaction Buffer, NEB) 2.5 µl, 10 mM dNTPs 0.5 µl, each primer, if added, 0.5 µl, Vent(exo-) polymerase (2 U/µl) 0.25 µl, Medfly genomic DNA 0.5 µl (20 ng) and water to final volume of 25 µl. Reactions were carried out either at 94° C. for 1 min; 26 cycles of 10 sec at 94° C., 30 sec at 58° C., 30 sec at 72° C., followed by a final extension step at 72° C. for 6 min or at 94° C. for 1 min; 26 cycles of 10 sec at 94° C., 20 sec at 58° C., 15 sec at 72° C., 15 sec at 58° C., 15 sec at 72° C., followed by a final extension step at 72° C. for 6 min. The primers added in reactions and the cycles used are shown in FIG. 5B.

The result is shown in FIG. 5B. The amplification in lane 4 shows stronger amplification band than normal PCR amplification in lane 1 and 2.

Example 2

Figure 6:
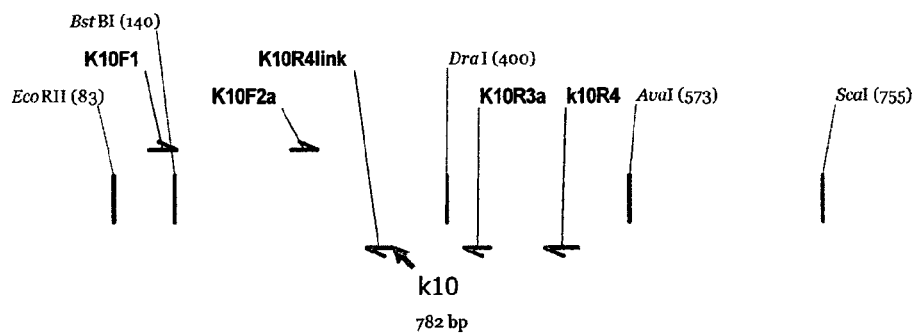
Figure 6:
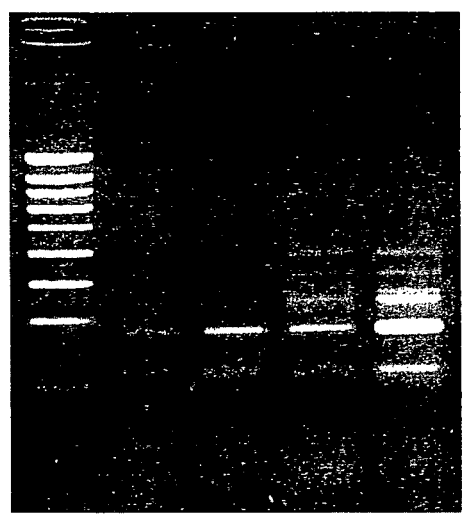

A reverse inner linker-primer K10R4link was designed, having sequence GGCTCATTAGGGCTCGTCATGTAAC-CTGAGGGTTAAATCTTCCCCATTG (SEQ ID NO:8). The first 25 nucleotides of K10R4link are identical to the sequence of K10F2A. Amplifications were performed using the same ingredients and conditions as in example 1, except the primers were added as indicated in the FIG. 6. The accumulated single stranded product is shown. The reaction with multiple primers and cycles promoting primer annealing to displacement strands give strong band intensity and multiple amplification bands(lane 4).

Example 3

Primers were designed to amplify a target DNA sequence BRAF gene from plasmids comprising a normal BRAF gene fragment. The sequence of this gene fragment comprises the sequence:

```
                                                    (SEQ ID NO: 9)
Ggaaagcatctcacctcatcctaacacatttcaagccccaaaaatcttaa aagcaggttatataggctaaatagaactaatcattgttttagacatactt attgactctaagaggaaagatgaagtactatgttttaaagaatattatat tacagaattatagaaattagatctcttacctaaactcttcataatgcttg ctctgataggaaaatgagatctactgttttcctttacttactacacctca gatatatttcttcatgaagacctcacagtaaaaataggtgatttggtct agctacagtgaaatctcgatggagtgggtcccatcagtttgaacagttgt ctggatccatttttgtggatggtaagaattgaggctattttccactgatt aaatttttggccctgagatgctgctgagttactagaaagtcattgaaggt ctcaactatagtattttcatagttcccagtattcac
```

The sequences of the primers are:

```
BrafF2
GGAAAGCATCTCACCTCATCCTAACAC          (SEQ ID NO: 10)

BrafEndR2
GACTTTCTAGTAACTCAGCAGCATCTCA         (SEQ ID NO: 11)

BraFAMR2
GGACCCACTCCATCG1GATTTC2A             (SEQ ID NO: 12)
```

Wherein "1" is dR-biotin, "2" is Phosphorothioate linkage. All nucleic acid sequences are written 5' to 3' unless otherwise stated. Herein BraFAMR2 is a linker-primer, dR-biotin is a blocking moiety.

Primers were diluted to a final concentration of 10 µM. Amplification was performed using the following ingredients and conditions: 10× Buffer (NEB) 2.5 µl, 10 mM dNTPs 0.5 µl, each primer, if added, 0.5 µl, Vent(exo-) DNA polymerase (5 U/µl) 0.25 µl, plasmid DNA 0.5 µl ($10^5$ molecules) and water to final volume of 25 µl. Reactions were carried out at 94° C. for 1 min; 40 cycles of 15 sec at 94° C., 30 sec at 57° C., 15 sec at 72° C. on BioMetra PCR machine. The primers added in reactions are as follows:

| Tube number | 1 | 2 | 3 | 4 |
|---|---|---|---|---|
| BrafF2 | + | + | + | + |
| BrafEndR2 | + | + | − | + |
| BrafFamR2 | − | + | + | − |
| Plasmid DNA | + | + | + | − |

The amplified DNA products were loaded in an agarose gel. DNA from tube number 2 showed single-stranded end product.

Example 4

The experiment described in this example shows a method of the present invention and a detection system as depicted in FIG. 3E.

A linker-primer K10R4tlong having a sequence GGTGGCGTTGCGGCTGGCGGAGCTCATTAGGGCTCGTCATGTAACCTGAGGGTTAAA TCTTCCCCATTG (SEQ ID NO:13) carries the 5' additional sequence GGTGGCGTTGCGGCTGGCGGAG (SEQ ID NO:14) at its 5' end which is not complementary or identical to the target sequence. A probe FamProbe having a sequence CTCCGCCAGCCGCAACGCCACCGCCAG (SEQ ID NO:15) with 5' Fam florescence dye comprises a sequence complementary to the additional sequence in K10R4tlong. The primer K10R4tlong also comprises a linker sequence CTCATTAGGGCTCGTCATGTAAC (SEQ ID NO: 16) which is complementary to a target sequence. A primer K10F2along having a sequence CACAGTTTATAGACCACCGACGGCTCATTAGGGCTCGTCATGTAAC (SEQ ID NO: 17) comprises a 3' end sequence identical to the linker-sequence in K10R4tlong. A probe K10F2aDab having a sequence GCACAGTTTATAGACCACCGACGG (SEQ ID NO:18) with 3' end labeled with DABCYL comprises sequence identical to the sequence at 5' end of primer K10F2along. Other primers used in this experiment include K10F1 and K10R3a which were used in example 1, and primer K10F1.5a having a sequence GCTGACTTCAAAACGAGAAGAGTTGC (SEQ ID NO:19).

Primers were diluted to a final concentration of 10 μM. Amplification was performed using the following ingredients and conditions: 10× Buffer (NEB) 2.5 μl, 10 mM dNTPs 0.5 μl, each primer, if added, 0.5 μl, Vent(exo-) DNA polymerase (5 U/μl) 0.25 μl, genomic DNA 0.5 μl and water to final volume of 25 μl. Reactions were carried out at 94° C. for 1 min; 40 cycles of 10 sec at 94° C., 15 sec at 56° C., 15 sec at 72° C., 15 sec at 56° C., 15 sec at 72° C. on BioRad Chromo4 real-time PCR machine. The primers added in reactions are as follows:

| Tube number | 1 | 2 | 3 | 4 | 5 | 6 | 7 | 8 |
|---|---|---|---|---|---|---|---|---|
| DNA | + | − | + | − | + | − | + | − |
| FamProbe | + | + | + | + | + | + | + | + |
| K10R4tlong | + | + | + | + | + | + | + | + |
| K10F2aDab | + | + | + | + | + | + | + | + |
| K10F2along | + | + | + | + | + | + | + | + |
| K10R3a | − | − | + | + | + | + | + | + |
| K10F1.5a | − | − | − | − | + | + | + | + |
| K10F1 | − | − | − | − | − | − | + | + |

Decreased fluorescence signals indicating amplified products were observed in tubes 1, 3, 5, and 7.

EQUIVALENTS

All publications, patent applications, and patents mentioned in this specification are indicative of the level of skill of those skilled in the art to which this invention pertains. Although only a few embodiments have been described in detail above, those having ordinary skill in the molecular biology art will clearly understand that many modifications are possible in the preferred embodiment without departing from the teachings thereof. All such modifications are intended to be encompassed within the following claims. The foregoing written specification is considered to be sufficient to enable those skilled in the art to which this invention pertains to practice the invention. Indeed, various modifications of the above-described modes for carrying out the invention which are apparent to those skilled in the field of molecular biology or related fields are intended to be within the scope of the following claims.

The invention claimed is:

1. A method for amplifying and optionally detecting a target sequence of a nucleic acid of interest in a sample, wherein the nucleic acid of interest comprises one strand or two separate complementary strands, the method comprising the steps of:
   (a) treating the sample with
      at least two oligonucleotide primers capable of hybridizing to a first strand of the target sequence,
      at least one oligonucleotide primer capable of hybridizing to a second strand of the target sequence complementary to the first strand,
      wherein the at least two primers for the first strand of the target sequence comprises one outer primer and one or more inner primers, wherein outer primer and inner primer hybridize to the first strand of the target sequence so that the 3' end of the outer primer points toward the 5' end of the inner primer,
      wherein the treating is carried out under hybridizing and extension conditions such that an extension product of each primer is synthesized complementary to its hybridizing strand of the target sequence if present;
   (b) separating the primer extension products from templates to produce single-stranded molecules;
   (c) treating the single-stranded molecules generated from step (b) with the primers of step (a) under hybridizing and extension conditions such that a primer extension product is synthesized using some or all of the single stranded molecules produced in step (b) as a template; and
   (d) repeating steps (b) and (c) at least once,
      wherein one or more of said inner primers is a linker-primer, which linker-primer comprises a linker so that a single-stranded end product is accumulated, wherein the outer primer or each outer primer is not a linker-primer, and wherein the extension conditions are such that the primer extension product of an inner primer is displaced by the primer extension product of an outer primer.

2. A method according to claim 1, wherein steps (b) and (c) are repeated at least twice.

3. A method according to claim 1, wherein said linker is a blocking moiety, wherein the replication of all or part of said linker-primer is blocked.

4. A method according to claim 3, wherein said blocking moiety is a hydrocarbon arm, nucleotide derivatives, non-nucleotide compound or a dye.

5. A method according to claim 3, wherein said blocking moiety is located at less than 3, 6, or 18 nucleotides away from 3' terminus of the linker primer.

6. A method according to claim 1, wherein said linker-primer comprises: (i) a priming portion capable of hybridizing to the first strand of the target sequence; and
   (ii) a linker sequence of nucleotides or non-nucleic acid 5' to the priming portion which is complementary or substantially complementary to a part of the second strand of the target sequence.

7. A method according to claim 6, wherein the linker sequence of the linker-primer comprises a sequence complementary or substantially complementary to a part of the sequence on the linker-primer extension product.

8. A method according to claim 6, wherein the linker sequence of the linker-primer comprises a sequence identical or substantially identical to the sequence of a primer for the second strand.

9. A method according to claim 1, wherein said linker comprises a cleavable moiety, wherein the linker-primer is a cleavable primer which is cleaved on the cleavable moiety or degraded completely or partially by an enzymatic agent when said linker-primer forms a hybrid with its complementary nucleic acid sequence.

10. A method according to claim 3 wherein the sample is treated with at least two primers capable of hybridizing to a second strand
    wherein the at least two primers for the second strand comprises one outer primer and one or more inner primers,
    wherein each inner primer hybridizes to the second strand 5' to the outer primer with respect to the second strand.

11. A method according to claim 8, wherein the linker sequence of the linker-primer comprises a sequence identical or substantially identical to the sequence of the or one inner primer for the second strand.

12. A method according to claim 8, wherein the linker sequence of the linker-primer comprises a sequence identical or substantially identical to the sequence of the or one of the outer primers for the second strand.

13. A method according to claim 1, wherein the hybridizing condition and the extension condition are either:

(i) the same condition; or (ii) different conditions, which are repeated at least once, and which are different temperatures.

14. A method according to claim 1, wherein the displacement is accomplished or promoted by an agent which promotes a strand displacement activity and\or wherein the primer extension activity and strand displacement activity are provided by a DNA polymerase, wherein the DNA polymerase is optionally a thermostable DNA polymerase which is optionally a Vent (exo-) DNA polymerase.

15. A method according to claim 1, wherein the separating the primer extension products from templates is accomplished by a combination of strand displacement during primer extension under the extension condition and denaturing.

16. A method according to claim 1 further comprising detecting the reaction products.

17. A method according to claim 16, wherein the detecting is real time detecting.

18. A method according to claim 16, wherein the detecting comprises detecting the single-stranded end product, which includes a stem-loop structure formed by the primer extension product.

19. A method according to claim 16, wherein the detecting is through a detection label which is comprised by the linker-primer or comprised by a detection probe attached with a detection label.

20. A method according to claim 19 wherein the detection label is a fluorescent or non-fluorescent dye which is attached to any nucleotide in the primer or probe.

21. A method according to claim 20, wherein the fluorescent dye is a fluorophore which is quenched or emits fluorescence upon hybridization of a primer or a probe to the primer extension product.

22. A method according to claim 19, wherein the detection probe hybridizes to a primer extension product wherein the hybridization brings two or more detection labels into close proximity or increases the distance between two or more detection labels such that they are no longer in close proximity.

23. A method for amplifying and optionally detecting a target sequence of a nucleic acid of interest in a sample, wherein the nucleic acid of interest comprises one strand or two separate complementary strands, the method comprising the steps of (a) treating the sample with two oligonucleotide primers capable of hybridizing to a first strand of the target sequence, and one oligonucleotide primer capable of hybridizing to a second strand of the target sequence complementary to the first strand, or with three oligonucleotide primers capable of hybridizing to a first strand of the target sequence, and one oligonucleotide primer capable of hybridizing to a second strand of the target sequence complementary to the first strand, or with two oligonucleotide primers capable of hybridizing to a first strand of the target sequence, and two oligonucleotide primers capable of hybridizing to a second strand of the target sequence complementary to the first strand, or with at least three oligonucleotide primers capable of hybridizing to a first strand of the target sequence, and at least two oligonucleotide primers capable of hybridizing to a second strand of the target sequence complementary to the first strand, wherein the treating is carried out under hybridizing and extension conditions such that an extension product of each primer is synthesized complementary to its hybridizing strand of the target sequence if present;

wherein the hybridizing condition and extension conditions are repeated at least once;

wherein the extension condition permits primer extension and strand displacement activity; and wherein the oligonucleotide primers cable of hybridising to a first strand of the target sequence comprise one outer primer and one or more inner primer %

(b) denaturing the primer extension products to produce single-stranded molecules;

(c) treating the single-stranded molecules generated from step (b) with the primers of step (a) under hybridizing and extension conditions such that a primer extension product is synthesized using some or all of the single stranded molecules produced in step (b) as a template, wherein the hybridization condition and extension condition are repeated at least once; wherein the extension condition permits primer extension and strand displacement activity;

and (d) repeating steps (b) and (c) at least once;

wherein the amplifying achieves more than two fold increase of the amount of the target nucleic acid sequence at each cycle through repeating steps (b) and (c), wherein the outer primer or each outer primer is not a linker-primer.

* * * * *